US 6,930,176 B2
United States Patent
Schofield et al.
(10) Patent No.: US 6,930,176 B2
(45) Date of Patent: Aug. 16, 2005

(54) MAJOR NEUTRALIZATION SITE OF HEPATITIS E VIRUS AND USE OF THIS NEUTRALIZATION SITE IN METHODS OF VACCINATION AND IN METHODS OF SCREENING FOR NEUTRALIZING ANTIBODIES TO HEPATITIS E VIRUS

(75) Inventors: Darren Schofield, Wantage (GB); Suzanne U. Emerson, Kensington, MD (US); Robert H. Purcell, Boyds, MD (US)

(73) Assignee: The United States of America as represented by the Secretary of the Department of Health & Human Services, Washington, DC (US)

( * ) Notice: Subject to any disclaimer, the term of this patent is extended or adjusted under 35 U.S.C. 154(b) by 83 days.

(21) Appl. No.: 10/148,737

(22) PCT Filed: Nov. 30, 2000

(86) PCT No.: PCT/US00/32614

§ 371 (c)(1),
(2), (4) Date: Jan. 27, 2003

(87) PCT Pub. No.: WO01/40270

PCT Pub. Date: Jun. 7, 2001

(65) Prior Publication Data

US 2003/0211463 A1 Nov. 13, 2003

Related U.S. Application Data

(60) Provisional application No. 60/167,490, filed on Dec. 1, 1999.

(51) Int. Cl.[7] .......................... C12P 21/08; A61K 39/00; A61K 39/395; A61K 39/42
(52) U.S. Cl. ................ 530/388.1; 424/141.1; 424/130.1; 424/134.1; 424/147.1; 424/149.1; 424/93.1
(58) Field of Search ............... 530/388.1; 424/141.1, 424/130.1, 134.1, 147.1, 149.1, 93.1

(56) References Cited

FOREIGN PATENT DOCUMENTS

| WO | 94/06913 A | 3/1994 |
|---|---|---|
| WO | 95/21858 A | 8/1995 |

OTHER PUBLICATIONS

H. Junken et al. *DNA inoculation with a plasmid vector carrying the hepatitis E virus structural protein gene induces immune response in mice.* VACCINE, 1997, vol. 15, No. 4, pp. 357–362.

D. J. Schofield et al. *Characterization of 17 Chimpanzee Monoclonal Antibodies (MABS) To Hepatitis E Virus (HEV) Open Reading Frame 2 (CAPSID) Protein Generated Using Phage Display, Epitope Masking And Repertoire Cloning.* American Journal of Tropical Medicine and Hygiene, 1999, vol. 61, No. 3, Suppl., ABSTRACT.

D. J. Schofield et al. *Identification By Phage Display and Characterization of Two Neutralizing Chimpanzee Monoclonal Antibodies to the Hepatitis E Virus Caspid Protein.* Journal of Virology Jun. 2000, vol. 74, No. 12, pp. 5548–5555.

*Primary Examiner*—James Housel
*Assistant Examiner*—Bao Qun Li
(74) *Attorney, Agent, or Firm*—Knobbe, Martens, Olson & Bear, LLP

(57) ABSTRACT

The invention describes the identification of major neutralization site of hepatitis E virus (HEV) and the use of this neutralization site in methods of vaccination and in methods of screening for neutralizing antibodies to HEV. The invention also describes the isolation and characterization of neutralizing chimpanzee monoclonal antibodies reactive to the neutralization site and the use of these antibodies in the diagnosis, treatment and prevention of HEV.

6 Claims, 12 Drawing Sheets

(a)

(b)

|  | FR1 | CDR1 | FR2 | CDR2 |
|---|---|---|---|---|
| EV#4 | EVQLLESGGGLVQPGGSLRLSCAASGFTFS | DSWMH | WVRQVPGKGLEWVS | RISSDGDSTRYADSVQG |
| EV#31 | ..............................| ..NHAI. | ....TSD......A | T..GG.GA.Y.P...K. |

|  | FR3 | CDR3 | FR4 |
|---|---|---|---|
| EV#4 | RFIISRDNAKNTLYLQMNSLRVEDAVYYCTR | SPQYCSTTRCDWIHYDY | WGQGTLVTVSS |
| EV#31 | ..T.....S..MV.........A.......AK | DVLNVFEAERNYGWSTGYSFDY | ......R...... |

HEV ORF2 | 0 100 200 300 400 500 600 700aa

SAR55 aa607
SAR55 aa578
SAR55 aa508
SAR55 aa408
SAR55 aa308
SAR55 aa208

(b)

MW (kD) | HEV#4 | HEV#31 | HAV#6 anti-Fab + protein G | Ch1441 pre-immune | Ch1441 post-immune protein G only | SAR55 truncations

```
                              aa578                          aa607
                              RVAISTYTTSLGAGPVSISAVAVLAPHSAL
Mexico   (M74506)¹            .........R......A...A.....R...
Uigh179  (D11092)²            ..............................
SAR55    (M80581)³            ............................V.
KS2-87   (L25595)⁴            ..........................T...
Madras   (X99441)⁵            ..............................
HEV037   (X98292)⁶            ................A.............
NE8L     (D10330)⁷            ..............................
Hetian   (L08816)⁸            ..............................
Hyderabad (U22532)⁹           ........................G.....
US2      (AF060669)¹⁰         ..............T.....G.........
Swine    (AF011921)¹¹         ..............T.....G.........
US1      (AF035437)¹²         ..............T.....G.........
```

[1] [Huang, 1992 #174]
[2] [Aye, 1992 #175]
[3] [Tsarev, 1992 #149]
[4] [Yin, 1994 #177]
[5] direct Genbank submission
[6] [Donati, 1997 #182]
[7] [Tam, 1991 #178]
[8] [Bi, 1993 #179]
[9] [Panda, 1995 #180]
[10] [Meng, 1997 #167]
[11,12] [Schlauder, 1998 #168]

FIG. 7A

HEV#4 heavy chain amino acid sequence (SEQ ID NO:1)

| | | | | |
|---|---|---|---|---|
| EVQLLESGGS | LVQPGGSLRL | SCAASGFTFS | DSWMHWVRQV | PGKGLEWVSR | 50
| ISSDGDSTRY | ADSVQGRFII | SRDNAKNTLY | LQMNSLRVED | TAVYYCTRSP | 100
| QYCSTTRCDW | IHYDYWGQGT | LVTVSS | | | 126

HEV#4 heavy chain nucleotide sequence (SEQ ID NO:5)

| | | | | |
|---|---|---|---|---|
| GAGGTGCAGC | TGCTCGAGTC | TGGGGGAAGC | TTAGTTCAGC | CGGGGGGGTC | 50
| CCTGAGACTC | TCCTGTGCAG | CCTCTGGATT | CACCTTCAGT | GATTCGTGGA | 100
| TGCACTGGGT | CCGCCAAGTC | CCAGGGAAGG | GGCTGGAGTG | GGTCTCACGT | 150
| ATCAGTAGTG | ATGGCGACAG | CACAAGATAC | GCGGACTCCG | TGCAGGGCCG | 200
| ATTCATCATC | TCCAGAGACA | ACGCCAAGAA | CACACTGTAT | CTGCAGATGA | 250
| ATAGTCTGAG | AGTCGAGGAC | ACGGCTGTGT | ATTATTGCAC | AAGATCGCCG | 300
| CAATATTGTA | GTACTACCAG | GTGCGACTGG | ATTCACTATG | ACTACTGGGG | 350
| CCAGGGGACC | CTGGTCACCG | TCTCCTCA | | | 378

HEV#4 light chain amino acid sequence (SEQ ID NO:2)

| | | | | |
|---|---|---|---|---|
| AELTQSPSSL | SASVGDRVTI | TCRASQDVGH | YLGWFQQKPG | QAPKRLIYAA | 50
| SNLQSGVPSR | FSGSGSGTEF | TLTISSLQPE | DFATYYCLQH | NSYPWTFGQG | 100
| TKLEIKRTVA | AP | | | | 112

HEV#4 light chain nucleotide sequence (SEQ ID NO:6)

| | | | | |
|---|---|---|---|---|
| GCCGAGCTCA | CCCAGTCTCC | ATCCTCACTG | TCTGCATCTG | TAGGAGACAG | 50
| AGTCACCATC | ACTTGTCGGG | CGAGTCAGGA | CGTTGGCCAT | TATTTAGGCT | 100
| GGTTTCAGCA | GAAACCTGGG | CAAGCCCCTA | AGCGCCTGAT | CTATGCTGCA | 150
| TCCAATTTGC | AGAGTGGGGT | CCCATCCAGG | TTCAGCGGCA | GTGGATCTGG | 200
| GACAGAATTC | ACTCTCACAA | TCAGCAGCCT | GCAGCCTGAA | GATTTTGCCA | 250
| CTTATTACTG | TCTACAACAT | AATAGTTACC | CTTGGACGTT | CGGCCAAGGG | 300
| ACCAAGCTGG | AAATCAAACG | AACTGTGGCT | GCACCATC | | 338

FIG. 7B

HEV#31 Heavy chain amino acid sequence (SEQ ID NO:3)

| | | | | | |
|---|---|---|---|---|---:|
| EVQLLESGGS | LVQPGGSLRL | SCAASGFIFS | NHAIHWVRQT | SDKGLEWVAT | 50 |
| ISGGGGATYY | PDSVKGRFTI | SRDNSKNMVY | LQMNSLRAED | TAVYYCAKDV | 100 |
| LNVFEAERNY | GWSTGYSFDY | WGQGTRVTVS | S | | 131 |

HEV#31 heavy chain nucleotide sequence (SEQ ID NO:7)

| | | | | | |
|---|---|---|---|---|---:|
| GAGGTGCAGC | TGCTCGAGTC | TGGGGGAGGC | TTGGTACAGC | CGGGGGGGTC | 50 |
| CCTAAGACTC | TCGTGTGCAG | CCTCTGGATT | CATCTTCAGC | AACCATGCCA | 100 |
| TACACTGGGT | CCGCCAGACT | TCAGACAAGG | GGCTGGAGTG | GGTCGCAACT | 150 |
| ATTAGTGGTG | GTGGTGGTGC | CACTTATTAT | CCAGACTCTG | TCAAGGGCCG | 200 |
| ATTCACCATC | TCCAGAGACA | ATTCGAAGAA | TATGGTGTAT | CTGCAGATGA | 250 |
| ACAGCCTGAG | AGCCGAGGAC | ACGGCCGTGT | ATTACTGTGC | GAAAGATGTT | 300 |
| TTAAATGTTT | TCGAGGCGGA | ACGAAACTAT | GGTTGGAGTA | CCGGGTACTC | 350 |
| CTTTGACTAC | TGGGGCCAGG | GAACCCGGGT | CACCGTCTCC | TCA | 393 |

HEV#31 light chain amino acid sequence (SEQ ID NO:4)

| | | | | | |
|---|---|---|---|---|---:|
| AELQMTQSPS | SLSASVGDRV | TITCRASHKM | YDYVSWYHQR | PGEAPRLLIY | 50 |
| AASTLQTGAP | TRFSGSGSGT | DFTLTIGGLQ | PEDFGTYYCQ | RAFGTQLTFG | 100 |
| GGTKVEIKRT | VAAPSSS | | | | 117 |

HEV#31 light chain nucleotide sequence (SEQ ID NO:8)

| | | | | | |
|---|---|---|---|---|---:|
| GCCGAGCTCC | AGATGACCCA | GTCTCCATCC | TCCCTGTCTG | CATCTGTGGG | 50 |
| AGACAGAGTC | ACTATTACAT | GCCGGGCGAG | TCACAAAATG | TACGACTATG | 100 |
| TGAGTTGGTA | TCACCAGAGA | CCGGGGGAAG | CCCCTAGGCT | CCTGATCTAT | 150 |
| GCCGCCTCAA | CCTTGCAAAC | TGGGGCCCCA | ACAAGGTTCA | GTGGCAGTGG | 200 |
| ATCTGGGACA | GACTTCACTC | TCACCATCGG | CGGTCTGCAA | CCTGAAGATT | 250 |
| TTGGAACATA | TTACTGTCAG | CGTGCTTTCG | GGACACAGCT | CACCTTCGGT | 300 |
| GGAGGGACCA | AGGTGGAGAT | CAAACGAACT | GTGGCTGCAC | CATCTTCTTC | 350 |
| A | | | | | 351 |

FIG. 8

γ1-chain sequence data

| Mab | CDR3 Sequence | VH gene family |
|---|---|---|
| HEV#4 | SPQYCSTTRCDWIHYDY | 3 |
| HEV#31 | DVLNVFEAERNYGWSTGYSFDY | 3 |
| EBL#1 | GNSLDY | 1 |
| EBL#2 | GMEYYDNWGKVFLDAFDL | 3 |
| EBL#3 | SEVGGSWYIDVESNWFDP | 1 |
| EBL#4 | EHWRQLDY | 6 |
| EBL#5 | GDPIEAMSGGSWIETFHH | 5 |
| EBL#8 | ILMFGVLNS | 4 |
| EBL#9 | DRRGDFDF | 6 |
| EBL#10 | GSNWNSFYYYMDV | 3 |
| EBL#16 | EQWRLYDS | 6 |
| EBL#33 | DREVYPWDTYFKPSYFDF | 3 |
| EBL#53 | SQWRALDL | 6 |
| EBL#56 | DRRWELEI | 6 |
| EBL#77 | GDHTGYVHYFDS | 4 |
| EBL#79 | VTMVGVLTD | 4 |
| EBL#89 | EGCSGLSCYGSFDR | 4 |

FIG. 9
(A)
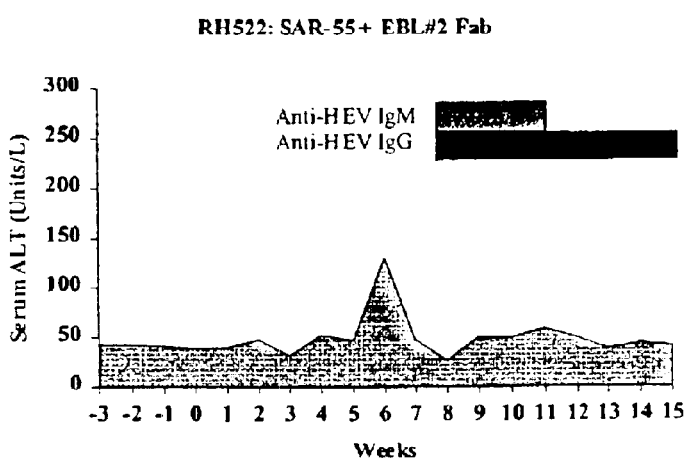
(B)
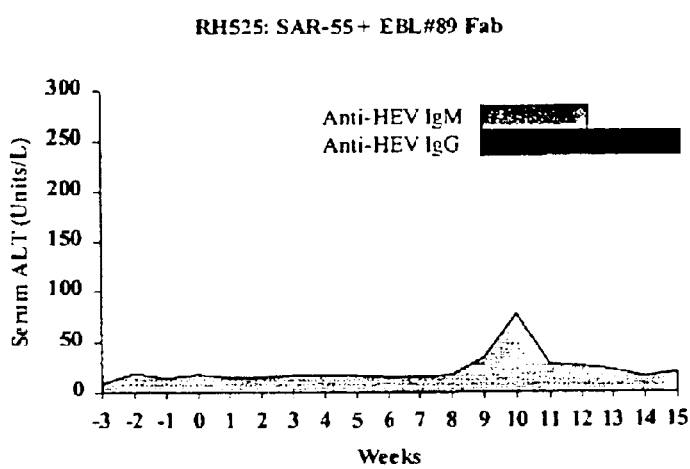
(C)
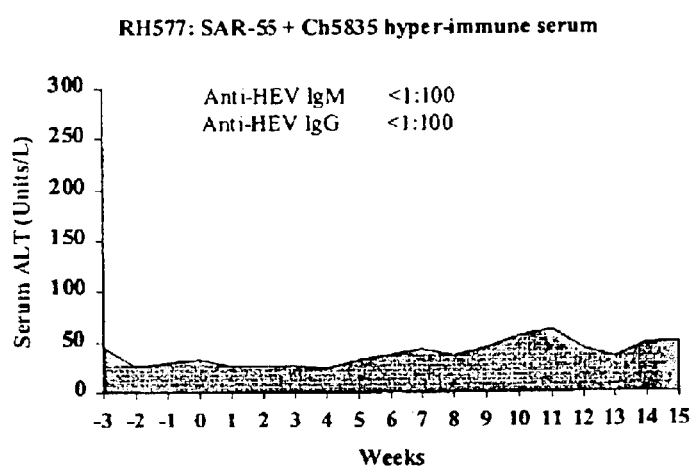

MAJOR NEUTRALIZATION SITE OF HEPATITIS E VIRUS AND USE OF THIS NEUTRALIZATION SITE IN METHODS OF VACCINATION AND IN METHODS OF SCREENING FOR NEUTRALIZING ANTIBODIES TO HEPATITIS E VIRUS

RELATED APPLICATIONS

This application represents the U.S. National Phase of International Application No. PCT/US00/32614 filed Nov. 30, 2000, designating the United States of America and published in English as WO 01/40270 on Jun. 7. 2001, which claims the benefit of priority of U.S. Provisional Application No. 60/167,490 filed Dec. 1, 1999.

FIELD OF THE INVENTION

The present invention relates to the identification of a major neutralization site of hepatitis E virus (HEV) and the use of this neutralization site in methods of vaccination and in methods of screening for neutralizing antibodies to HEV. The invention further relates to the isolation and characterization of neutralizing antibodies reactive to the neutralization epitope and the use of these antibodies in the diagnosis, treatment and prevention of HEV.

BACKGROUND OF THE INVENTION

Hepatitis E is endemic in many countries throughout the developing world, in particular on the continents of Africa and Asia. The disease generally affects young adults and has a very high mortality rate, up to 20%, in pregnant women (Mast, 1993; Tsega, 1992; Khuroo, 1981). The causative agent, hepatitis E virus (HEV), is transmitted primarily by the fecal-oral route, often through contaminated water (Purcell, 1996)). The availability of sensitive serological tests for HEV has permitted detailed assessment of the prevalence of HEV infection. In regions where HEV is endemic, anti-HEV antibodies have been detected in sera from convalescent individuals as well as from the general population. Surprisingly, in industrialized countries, such as the United States, where hepatitis E is not endemic, a significant proportion of healthy individuals within the general population are seropositive (up to 20% in some areas (Thomas, 1997; Mast, 1997)). However, clinical hepatitis E is rare in these countries and individuals usually acquire their infection during travel to a region that is endemic or epidemic for HEV.

It has been suggested that animals serve as reservoirs for HEV in some regions, and human infections may, in part, be zoonoses. There have been several reports of HEV-specific antibody (anti-HEV) in animals (Clayson, 1995; Karetnyi, 1993; Arankalle, 1994; Kabrane-Lazizi, 1999). Furthermore, an HEV-like virus was recently isolated from naturally infected swine in the United States (Meng, 1997). The four genotypes of HEV identified based on nucleotide sequence diversity are Asian/African, Mexican, U.S. and the New Chinese. To-date, only one serotype of HEV has been found. Therefore, it may be possible to produce a broadly protective vaccine in the near future.

Studies have shown that passively transferred anti-HEV significantly reduced virus shedding in feces, and abrogated disease in non-human primates challenged with a high dose of HEV (Tsarev, 1994). The findings suggest that immunoglobulin preparations, similar to those used for protection against hepatitis A, would be efficacious against hepatitis E. Field studies in India performed using pools of normal serum immunoglobulin collected from HEV endemic regions did not show protection from HEV infection or disease (Joshi, 1985; Khuroo, 1992; Zhuang, 1991). It is likely that the titer of anti-HEV antibodies in those studies was too low to have a protective effect. As pooled normal human serum is unlikely to be useful as an immunoprophylactic reagent against HEV, neutralizing monoclonal antibodies to HEV could be used to produce a high titer immunoglobulin preparation which might protect against hepatitis E virus.

Antibody phage display libraries provide a powerful tool for the isolation of human antibodies to important viral pathogens. Antibody phage display libraries are constructed from variable heavy and light chain antibody genes using a phage display vector specifically designed for the expression of antibody fragments to an antigen (Winter, 1994; de Kruif, 1996; Burton, 1994). From such libraries, large numbers of human monoclonal antibodies to an antigen of choice can be cloned and isolated. The technique provides new opportunities to produce high affinity human monoclonal antibodies for use in passive immunoprophylaxis. To date, monoclonal antibodies to a number of viral antigens, for example, human immunodeficiency virus-1 gp120 (Thompson, 1996; Geoffroy, 1994; Burton, 1991; Ditzel, 1997), measles virus (Bender, 1994), and respiratory syncitial virus F protein (Crowe, 1994), have been isolated.

The identification of neutralization epitopes of HEV provides an alternative method for the production of neutralizing antibodies to HEV.

SUMMARY OF THE INVENTION

The present invention relates to the identification of a neutralization site of hepatitis E virus (HEV) which consists of one or more neutralization epitopes of HEV. The neutralization site is a polypeptide about 30 amino acids in length spanning from amino acids 578 to 607 of the ORF2 gene (capsid gene) of HEV. The neutralization site is conserved among genetically divergent HEV strains.

The invention also relates to the use of the neutralization site or the epitope(s) contained within the neutralization site as an immunogen to elicit the production in mammals of antibodies that can effectively neutralize one or more strains of HEV.

The invention also relates to the use of the neutralization site or the epitope(s) contained within the neutralization site as vaccine to effectively prevent, and/or reduce the incidence of HEV infection. An epitope or antigenic determinant is typically about six amino acid residues.

The invention also relates to pharmaceutical compositions comprising the neutralization site or the epitope(s) contained within the neutralization site.

The invention further relates to methods of producing neutralizing antibodies to HEV comprising administering the pharmaceutical compositions of the invention to a mammal in an amount effective to stimulate the production of neutralizing antibodies to HEV.

The present invention also relates to the isolation and characterization of two neutralizing chimpanzee monoclonal antibodies which are reactive with the neutralization site or the epitope(s) contained within the neutralization site of the invention. These monoclonal antibodies react with genetically divergent HEV strains.

The invention also relates to the heavy and light chain immunoglobulin variable region amino acid sequences of these neutralizing monoclonal antibodies to HEV, and to the nucleic acid molecules encoding the amino acid sequences.

The present invention also relates to the use of the neutralizing monoclonal antibodies of the invention in the detection of HEV infection in animals, especially mammals, and most especially humans.

The neutralizing monoclonal antibodies of the present invention are particularly advantageous for use in the development of prophylactic, therapeutic and diagnostic agents for the prevention and treatment of hepatitis E and detection of human HEV.

The invention therefore also relates to pharmaceutical compositions which comprise the neutralizing antibodies of the invention.

BRIEF DESCRIPTION OF THE FIGURES

FIG. 3 shows the result of a radioimmunoprecipitation assay using monoclonal antibodies HEV#4 and #31. FIG. 3(a) shows a schematic representation of the ORF2 proteins truncated at the C-terminus. FIG. 3(b) shows an autoradiograph of the radioimmunoprecipitation assay using a pool of the six $^{35}$S-labeled ORF2 truncation products.

FIG. 4 shows an ELISA assay testing the crossreactivity of HEV#4 and HEV#31 with recombinant baculovirus-expressed ORF2 protein from the Pakistani (SAR-55) and swine HEV strains.

FIG. 6 shows a comparison of amino acid residues 578 to 607 of the ORF2 protein from different HEV strains.

FIG. 7(a) shows the heavy and light chain immunoglobulin variable region amino acid sequences of HEV#4 and the nucleotide sequences encoding the amino acid sequences. FIG. 7(b) shows the heavy and light chain immunoglobulin variable region amino acid sequences of HEV#31 and the nucleotide sequences encoding the amino acid sequences.

FIG. 8 shows the CDR3 sequences of the γ1-heavy chain of 17 monoclonal antibodies including HEV#4 and HEV#31 isolated from the phage display library.

FIG. 9 shows in vitro neutralization of HEV with in vivo monitoring in rhesus monkeys inoculated with HEV (SAR-55 strain) treated with (a) EBL#2 Fab, (b) EBL#89 Fab, and (c) chimpanzee Ch5835 hyper-immune serum.

DETAILED DESCRIPTION OF THE INVENTION

Figure 1:
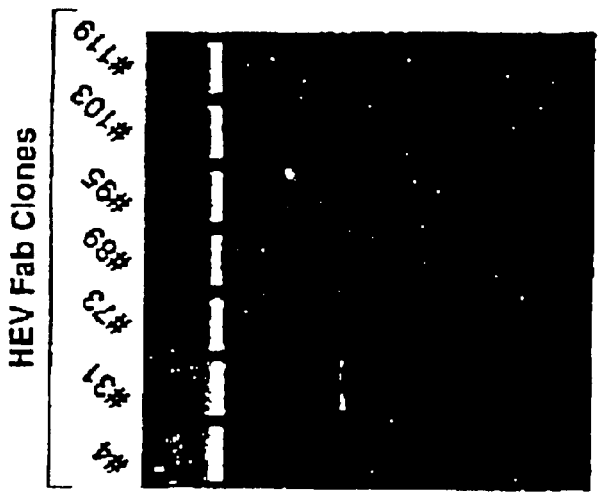
FIG. 1(a) shows restriction fragment analysis of seven HEV-specific Fab clones. Plasmid DNA was digested with Bst N1 and an aliquot was electrophoresed on a 3% agarose gel.
FIG. 1(b) shows the amino acid sequence of the γ1-chains of monoclonal antibodies HEV#4 and #31.

The present invention relates to a peptide of at least 30 amino acids in length, spanning amino acids 578 to 607 of the open-reading frame 2 gene (capsid gene) of hepatitis E virus (HEV), which has been identified as a neutralization site of the virus.

The results described herein show that the peptide comprising amino acid 112 to amino acid 578 of the open-reading frame 2 gene reacted weakly with the neutralizing antibodies to HEV compared to the peptide comprising amino acid 112 to amino acid 607 which reacted strongly with the neutralizing antibodies to HEV. As the negative result obtained with the peptide comprising amino acid 112 to amino acid 578 may be due to a disruption of a neutralization epitope at the amino terminus of the 578–607 sequence, it is understood that the polypeptide of the invention may extend 5–10 amino acids amino-terminal to amino acid 578 such that it encompasses from about amino acid 572, or 573 to about amino acid 607, more preferably, from about amino acid 568 to about amino acid 607 of the open-reading frame 2 gene.

It is further understood that the neutralization site consists of one or more neutralization epitopes of HEV. The nature and the location of the neutralization epitope(s) within the neutralization site can be determined by deletional or mutational analyses described herein. A neutralization epitope is understood to be composed of at least 6 amino acids, preferably 6 to 8 amino acids.

As the neutralization site is conserved among genetically divergent HEV strains, it is understood that although the neutralization site of the invention was identified as a polypeptide about 30 amino acids in length spanning from amino acids 578 to 607 of the ORF2 gene of HEV strain SAR-55, the invention also encompasses a neutralization site and epitope(s) from corresponding regions of the ORF2 gene of other HEV strains.

It is further understood that substitution of amino acid residue(s) within the neutralization site or neutralization epitope(s) of the invention may result in polypeptides which have similar neutralization properties as the neutralization site or the neutralization epitope(s) set forth above, and which are capable of directing the production of antibodies that are reactive with the neutralization site or epitope(s) of the invention described above. It should be noted that the neutralization site set forth above represents a preferred embodiment of the present invention.

Deletional or mutational studies of the neutralization site of the invention will allow the engineering of broadly reactive neutralization epitopes of HEV. Such studies will also allow the engineering of genotype-specific epitopes of HEV which are useful as diagnostic agents for various genotypes of HEV.

The invention also relates to the use of the neutralization site or the neutralization epitope(s) of the invention as an immunogen to elicit the production in mammals of antibodies that can effectively neutralize one or more strains of HEV.

The term "antibodies" is used herein to refer to immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', F(ab')$_2$, F$_d$ and F(v) as well as chimeric antibody molecules.

In one embodiment, the neutralizing antibodies are produced by immunizing a mammal with a peptide or peptide fragments encoding the neutralization site or the neutralization epitope(s) of the invention. In another embodiment, the neutralizing antibodies are produced by immunizing a mammal with nucleic acids encoding the neutralization site or the neutralization epitope(s) of the invention. In yet another embodiment, the neutralizing antibodies are produced by immunizing a mammal with peptides bridging the ORF2 region of HEV. The antibody molecules may then be collected from the mammal if they are to be used in immunoassays or for providing passive immunity.

The antibody molecules of the present invention may be polyclonal or monoclonal. Monoclonal antibodies may be produced by methods known in the art. Portions of immunoglobulin molecules may also be produced by methods known in the art.

The antibody of the present invention may be contained in various carriers or media, including blood, plasma, serum (e.g., fractionated or unfractionated serum), hybridoma supernatants and the like. Alternatively, the antibody of the present invention is isolated to the extent desired by well known techniques such as, for example, by using DEAE SEPHADEX, or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibodies of the IgG class are preferred for purposes of passive protection.

In addition to its use in generating neutralizing antibodies to HEV, the neutralization site or the neutralization epitope(s) of the invention can be used as an immunogen to stimulate the production of a protective humoral and/or cellular immune response to HEV.

In one embodiment, the immunogen may be a partially or substantially purified peptide or peptide fragments encoding the neutralization site or the neutralization epitope(s) of the invention. In another embodiment, the immunogen may be a construct in which the peptide or peptide fragments of the invention is incorporated into a live virus vector, for example, a vaccinia virus or adenovirus vector, which may contain neutralization epitopes of other pathogens. In yet another embodiment, the immunogen may be a construct in which the peptide or peptide fragments of the invention is incorporated into proteins such as the hepatitis B surface antigen or the hepatitis B core antigen. In another embodiment, the immunogen may be a construct in which the peptide or peptide fragments of the invention is incorporated into a mosaic protein which contains antibody binding site(s) of other antigens. In another embodiment, the immunogen may be a cell, cell lysate from cells transfected with a recombinant expression vector, or a culture supernatant containing the peptide encoding the neutralization site or the neutralization epitope(s) of the invention. In another embodiment, the immunogen may be a DNA construct encoding the neutralization site or the neutralization epitope(s) of the invention.

While it is possible for the immunogen to be administered in a pure or substantially pure form, it is preferable to present it as a pharmaceutical composition, formulation or preparation. For example, the immunogen can be used in a suitable diluent such as saline or water, or complete or incomplete adjuvants. In a preferred embodiment, the immunogen is coupled to a carrier to make the peptide more immunogenic. Examples of such carrier molecules include but are not limited to bovine serum albumin (BSA), keyhole limpet hemocyanin (KLH), tetanus toxoid, and the like. The immunogen can be administered by any route appropriate for antibody production such as intravenous, intraperitoneal, intramuscular, subcutaneous, and the like.

The effective amount of peptide per unit dose sufficient to induce an immune response depends, among other things, on the species of mammal inoculated, the body weight of the mammal and the chosen inoculation regimen, as well as the presence or absence of an adjuvant, as is well known in the art. Inocula typically contain peptide concentrations of about 1 microgram to about 50 milligrams per inoculation (dose), preferably about 10 micrograms to about 10 milligrams per dose, most preferably about 100 micrograms to about 5 milligrams per dose.

The term "unit dose" as it pertains to the inocula refers to physically discrete units suitable as unitary dosages for mammals, each unit containing a predetermined quantity of active material (polypeptide) calculated to produce the desired immunogenic effect in association with the required diluent.

The immunogen may be administered once or at periodic intervals until a significant titer of anti-HEV antibody is produced. The antibody may be detected in the serum using an immunoassay.

To monitor the antibody response of individuals administered the compositions of the invention, antibody titers may be determined. In most instances it will be sufficient to assess the antibody titer in serum or plasma obtained from such an individual. Decisions as to whether to administer booster inoculations or to change the amount of the composition administered to the individual may be at least partially based on the titer.

The titer may be based on an immunobinding assay which measures the concentration of antibodies in the serum which bind to the neutralization site or the neutralization epitope(s) contained within the neutralization site of the invention. The ability to neutralize in vitro and in vivo biological effects of the viruses of this invention may also be assessed to determine the effectiveness of the immunization.

Where immunoassays are involved, such kits may contain a solid support, such as a membrane (e.g., nitrocellulose), a bead, sphere, test tube, microtiter well, rod, and so forth, to which a receptor such as an antibody specific for the target molecule will bind. Such kits can also include a second receptor, such as a labeled antibody. Such kits can be used for sandwich assays. Kits for competitive assays are also envisioned.

The invention also relates to the use of the immunogens of the present invention as vaccines for either a prophylactic or therapeutic purpose. When provided prophylactically, a vaccine(s) of the invention is provided in advance of any exposure to any one or more of the HEV strains or in advance of any symptoms due to infection of the viruses. The prophylactic administration of a vaccine(s) of the invention serves to prevent or attenuate any subsequent infection of these viruses in a mammal. When provided therapeutically, a vaccine(s) of the invention is provided at (or shortly after) the onset of infection or at the onset of any symptom of infection or any disease or deleterious effects caused by these viruses. The therapeutic administration of the vaccine(s) serves to attenuate the infection or disease. The vaccine(s) of the present invention may, thus, be provided either prior to the anticipated exposure to the viruses of this invention or after the initiation of infection.

The immunogens of the invention may be supplied in the form of a kit, alone, or in the form of a pharmaceutical composition.

The present invention also relates to neutralizing chimpanzee monoclonal antibodies to HEV, where the antibodies are isolated as Fab fragments from a phage display library prepared from RNA isolated from bone marrow lymphocytes of a chimpanzee experimentally infected with the HEV strain SAR-55, the hepatitis A virus (HAV), the hepatitis B virus (HBV), the hepatitis C virus (HCV), and the hepatitis D virus (HDV).

The present invention thus relates to neutralizing chimpanzee monoclonal antibodies having specified heavy (H) and light (L) chain immunoglobulin variable region amino acid sequences in pairs (H:L) which confer the ability to bind to the neutralization epitope of the invention.

The present invention therefore relates to the heavy chain immunoglobulin variable region amino acid sequences and the light chain immunoglobulin variable region amino acid sequences shown in FIG. 7.

The present invention also relates to nucleic acid molecules encoding the heavy and light chain immunoglobulin variable region amino acid sequences of this invention where these sequences are shown in FIG. 7.

Of course, due to the degeneracy of the genetic code, variations are contemplated in the sequences shown in FIG. 7 which will result in nucleic acid sequences that are capable of directing production of antibodies that are identical to the antibodies of the invention. It should be noted that the DNA sequences set forth above represent a preferred embodiment of the present invention.

The invention further relates to methods of making neutralizing chimpanzee monoclonal antibodies from the phage display library described herein. In a preferred embodiment, the method for isolating a neutralizing monoclonal antibody from the phage display library involves (1) using immunoaffinity techniques such as panning to select phage particles that immunoreact with the neutralizationepitope of the invention; (2) infecting bacteria with the selected phage particles; (3) preparing and analyzing the phagemid DNA from the colonies recovered; and (4) expressing and purifying soluble Fab fragments from clones of interest for further analysis.

The invention also relates to the use of the neutralizing monoclonal antibodies as diagnostic agents.

The antibodies can be used as an in vitro diagnostic agent to test for the presence of HEV in biological samples. In one embodiment, a sample such as biological fluid or tissue obtained from an individual is contacted with a diagnostically effective amount of one or more of the human monoclonal antibodies of this invention under conditions which will allow the formation of an immunological complex between the antibody and the HEV antigen that may be present in the sample. The formation of an immunological complex, which indicates the presence of HEV in the sample, is then detected by immunoassays. Such assays include, but are not limited to, radioimmunoassays, Western blot assay, immunofluorescent assay, enzyme immunoassay, chemiluminescent assay, immunohistochemical assay and the like.

The invention also relates to the use of the monoclonal antibodies of the invention in passive immunoprophylaxis and passive immunotherapy of HEV infection.

When used in passive immunotherapy, the patient is administered a therapeutically effective amount of one or more neutralizing human monoclonal antibodies. The passive immunotherapy of this invention may be practiced on individuals infected with HEV; passive immunoprophylaxis may be practiced on individuals at risk of HEV infection.

A prophylactically or therapeutically effective amount of a monoclonal antibody for individual patients may be determined by titrating the amount of antibody given to the individual to arrive at the therapeutic or prophylactic effect while minimizing side effects. The effective amount can be measured by serological decreases in the amount of HEV antigens in the individual. The plasma concentration for individuals receiving the treatment is typically between 0.1 ug/ml to 100 ug/ml.

The monoclonal antibodies of this invention may be administered via one of several routes including, but not limited to intravenous, intraperitoneal, intramuscular, subcutaneous, transdermal and the like.

The present invention therefore relates to pharmaceutical compositions comprising at least one antibody of the invention and a pharmaceutically acceptable carrier where such carriers may include physiologically acceptable buffers, for example, saline or phosphate buffered saline.

The present invention further relates to anti-idiotypic antibodies to the monoclonal antibodies of this invention. In one embodiment, an anti-idiotypic antibody can be prepared by immunizing a host animal with a monoclonal antibody of this invention by methods known to those of skill in the art. To eliminate an immunogenic response to the Fc region, antibodies produced by the same species as the host animal can be used or the Fc region of the administered antibodies can be removed. The anti-idiotypic antibodies produced can be used to prepare pharmaceutical compositions rather than using the monoclonal antibodies of this invention.

The present invention includes compositions of the antibodies described above, suitable for parenteral administration including, but not limited to, pharmaceutically acceptable sterile isotonic solutions. Such solutions include, but are not limited to, saline and phosphate buffered saline for intravenous, intramuscular, intraperitoneal, or subcutaneous injection, or direct injection into a joint or other area.

In providing the antibodies of the present invention to a recipient mammal, preferably a human, the dosage of administered antibodies will vary depending upon such factors as the mammal's age, weight, height, sex, general medical condition, previous medical history and the like.

In general, it is desirable to provide the recipient with a dosage of antibodies which is in the range of from about 5 mg/kg to about 20 mg/kg body weight of the mammal, although a lower or higher dose may be administered. In general, the antibodies will be administered intravenously (IV) or intramuscularly (IM).

The present invention will now be described by way of examples, which are meant to illustrate, but not limit, the scope of the invention.

EXAMPLE

Materials and Methods

Donor Animal

Bone marrow was aspirated from the iliac crest of chimpanzee 1441. The animal had been experimentally infected with HAV, HBV, HCV, HDV and HEV. Prior to the aspirate being taken, the animal was boosted with the commercial HAV vaccine (HAVRIX, SmithKline Beecham), HBV vaccine (Engerix-B, SmithKline Beecham), and purified baculovirus-expressed HEV ORF2 protein. The bone marrow lymphocytes were separated on a Ficoll gradient and stored as a viable single cell suspension in 10% dimethyl sulfoxide, 10% fetal calf serum and RPMI 1640 medium (BioWhittaker) in liquid nitrogen.

Construction of γ1/κ Antibody Phase Library

Total RNA was extracted from ~10 bone marrow lymphocytes (RNA Isolation Kit; Stratagene) and mRNA was reverse transcribed into cDNA using an oligo (dT) primer (Gibco/BRL). The cDNAs were amplified by PCR using rTth DNA polymerase (Perkin Elmer). Thirty cycles of 94° C. for 15 s, 52° C. for 50 s, and 68° C. for 90 s were performed. Chimpanzee κ-chain genes were amplified using primers specific for the human κ-chain genes. Fd segments (variable and first constant domains) of the chimpanzee γ1-chain genes were amplified with nine family-specific human VH primers recognizing the 5' end of the genes [Barbas, 1991; Persson, 1991 and a chimpanzee γ1-specific3'primer(5'-GCATGTACTAGTTGTGTCACAAGATTTGGG-3') (SEQ ID NO: 33) (3' primer sequence determined from Vijh-Warrier et al. [Vijh-Warrier, 1995]).

The amplified κ-chains were cloned into the pComb3H phage display vector as described by Williamson et al. [Williamson, 1993]. The amplified γ1-chains were cloned into pGEM-T cloning vector (Promega) via the additional adenosine nucleotide added by the rTth DNA polymerase at the 3' ends of the PCR product. The γ1-pGEM-T clones were transformed into *Escherichia coli* XL-1 Blue (Stratagene) and expanded into a volume of 2 liters by solid phase amplification as described in Glamann et al. [Glamann, 1998]. The γ1-pGEM-T library was digested with Xho I and Spe I (Boehringer Mannheim), and ligated into the κ-chain pComb3H library, also digested with Xho I and Spe I. The ligated products were transformed into *E.coli* XL-1 Blue. Transformants were expanded into a volume of 2 liters by solid phase amplification. The final library of $1.9 \times 10^7$ clones was stored in 12.5% glycerol-LB broth at −80° C. until use.

Panning and ELISA Reagents

HEV ORF 2 proteins (55 kD) from the Pakistani strain SAR-55, and swine HEV were produced in baculovirus and purified according to Robinson et al. [Robinson, 1998]. In all panning and enzyme-linked immunosorbant assay (ELISA) experiments, HEV ORF 2 proteins were diluted to 1.0 μg ml$^{-1}$ in 50 mM sodium carbonate buffer (pH 9.6), and adsorbed to EIA/RIA A/2 (ELISA) plates (Costar) overnight at 4° C. A goat anti-human IgG (H+L)-specific antibody (Pierce) was used to detect Fab production. This was coated to microtiter wells at a dilution of 1:1000, in 50 mM sodium carbonate buffer (pH 9.6), as above.

Library Screening

Screening of the combinatorial library was carried out according to the method described by Barbas et al. [Barbas, 1991] and Williamson et al. [Williamson, 1993]. Approximately $10^9$ bacteria from the library stock were inoculated into Luria-Bertani (LB) broth (Gibco/BRL) supplemented with 100 μg ml$^{-1}$ ampicillin and 1% (v/v) glucose (Sigma), and grown up and infected with helper phage, VCS M13 (Stratagene), at a multiplicity of infection of 50, to produce the library displayed on the surface of phage particles. Phage were panned on HEV ORF2-coated ELISA wells; in all, four rounds of panning were performed. After amplification of the selected library, the phagemid DNA was extracted and the vector modified by restriction enzyme digestion to remove the bacteriophage coat protein III-encoding region of the phage [Bender, 1993]. The phagemid DNAs were religated and transformed into *E.coli* XL-1 Blue to allow soluble Fabs to be produced. Colonies were inoculated into individual wells of microtiter plates and grown in LB broth at 30° C. overnight. Fab production was induced according to Glamann et al. [Glamann, 1998], and the bacterial supernatants tested by ELISA for reactivity with HEV ORF2 and for the presence of Fab.

Fab Production and Purification

Fab purification was facilitated by modification of the vector, pComb3H, to encode a six-histidine tail at the end of the soluble Fab fragment (modification carried out by, and detailed in Glamann et al. [Glamann, 1998]). Bacterial culture and Fab fragment purification were carried out as described by Glamann et al. [Glamann, 1998]. Protein concentrations were determined by both dye binding assay (Bio-Rad) and $A_{280nm}$ (using the extinction coefficient of 1.4 optical density units equivalent to 1.0 mg ml$^{-1}$). The Fab purity was determined by polyacrylamide gel electrophoresis with colloidal Coomassie blue staining (Sigma).

ELISA Analysis of Fab Reactivity and Cross-reactivity

Protein antigens were coated onto ELISA microtiter plates at 1.0 μg ml$^{-1}$ (HEV ORF2 protein) or 10.0 μg ml$^{-1}$ (thyroglobulin, lysozyme, and cytochrome C (Sigma)). Antigen-coated wells were blocked for 1 h at room temperature with 3% bovine serum albumin (BSA)-PBS, washed twice with PBS-Tween 20 (0.05 % (v:v)), and 50 μl of crude or purified Fab was added to the wells. After 1 h incubation at 37° C., the plates were washed six times with PBS-Tween 20. Bound Fab were detected with 1:1500 dilution of a goat anti-human F(ab')$_2$ alkaline phosphatase labeled secondary antibody (Pierce). The assay color was developed using 1 mg ml$^{-1}$ p-nitrophenyl phosphate (Sigma) in diethanolamine buffer (Pierce). Optical density was determined at 405 nm with a reference wavelength of 650 nm.

Nucleic Acid Sequencing, Analysis and Bst N1 Fingerprinting of HEV-specific Fab Clones Nucleic acid sequencing was performed with the ABI PRISM Dye Terminator Cycle Sequencing Ready Reaction kit by using Ampli-Taq DNA Polymerase (Perkin-Elmer) and the following sequencing primers: heavy chain, 5'-ATTGCCTAC-GGCAGCCGCTGG-3' (HC1) (SEQ ID NO: 34) and 5'-GGAAGTAGTCCTTGACCAGGC-3' (SEQ ID NO: 35) (HC4); κ chain, 5'-ACAGCTATCGCGATTGCAGTG-3' (SEQ ID NO: 36) (LC1) and 5'-CACCTGATCCTCAGATGGCGG-3' (SEQ ID NO: 37) (LC4) [Glamann, 1998]. The resulting sequences were analyzed using GeneWorks (Oxford Molecular Group) software package. Sequence similarity searches were performed using the V-BASE prograsn, which is a compilation of all the available human variable segment Ig germ line sequences [Cook, 1995]. For Bst N1 (New England Biologicals) fingerprinting, one microgram of plasmid DNA was digested with 1 U of enzyme overnight at 60° C. The restriction patterns were analyzed on a 3% agarose gel.

Western Blotting

HEV ORF2 protein was heated in 2× Laemelli buffer [Laemelli, 1970] and run in a single well 10% polyacrylamide gel (Novex). Electrophoretic transfer of the protein to a nitrocellulose membrane was carried out at 250 mA for 1 h at 4° C. The membrane was blocked for 30 min with 5% skimmed milk in PBS prior to overnight incubation with equal concentrations of purified of HEV#4 and HEV#31, or a 1:100 dilution of chimpanzee 1441 serum, at 4° C. After 6 of 10 min washes each, anti-human IgG (Fab-specific) alkaline phosphatase-labeled (Pierce) secondary antibody was added at a dilution of 1:5000 in 5% skimmed milk-PBS. After 1 h, the blot was washed, and NBT/BCIP substrate (Pierce) added.

Affinity Determinations Using BIAcore™

The gold-coated sensor chips, CM-5, are coated with a carboxylated dextran polymer matrix to which the HEV ORF2 protein was amine coupled (Pharmacia Biosensor).

The carboxyl groups on the dextran surface were activated with 35 μl of a 50:50 (v/v) solution of N-hydroxylsuccinamide (NHS) and N-ethyl-N'-(3-diethylaminopropyl) carbodiimide (EDC). HEV ORF2 protein was diluted in 10 mM sodium acetate (pH 4.5) prior to coupling. After washing the sensor surface with HBS [10 mM HEPES (pH 7.5), 0.15 M NaCl, 3.4 mM EDTA, 0.05% Tween 20], the remaining active binding sites on the chip were blocked by the addition of ethanolamine hydrochloride.

Affinity measurements were made using three different coating concentrations of HEV ORF2 protein, one for each flow cell on the chip, with the fourth flow cell left uncoated and blocked as a control. The affinity measurements were initiated by passing HBS over the sensor surface for 100 s at 10 μl min$^{-1}$ then 50 μl of Fab was injected at the same flow rate. The kinetic analysis was performed twice. The first chip was coated with 37 Resonance Units (RU), 203 RU and 334 RU of HEV ORF2 protein. The second chip was coated with 363 RU, 225 RU and 106 RU of HEV ORF2 protein Serial dilutions of HEV#4 and HEV#31 were made in HBS buffer. Eight dilutions of each monoclonal antibody were tested over the sensor surfaces; the HEV#4 dilutions ranged from 0.5 to 200 nM, and HEV#31 from 1.0 to 400 nM. Between each monoclonal antibody binding phase the sensor surface was regenerated with a one minute pulse of regeneration buffer [1 M NaCl, 50 mM NaOH]. The level of monoclonal antibody binding to the sensor surface was reproducible following regeneration.

Fab Biotinylation and Indirect Competition ELISA

Prior to biotinylation, purified HEV#4 and HEV#31 were dialyzed against PBS overnight at 4° C. Conjugation with biotin was carried out as per the manufacturer's instructions (Pierce). The biotinylated Fabs were titrated on HEV ORF2-coated wells to determine a dilution that was sub-saturating and gave an O.D. reading of approximately 1.0 at $A_{405nm}$. For the competition assay, three-fold dilutions of unlabeled and unpurified Fab were incubated on HEV ORF2-coated wells for 1 h at 37° C., then washed four times with PBS-Tween 20. A single dilution of biotinylated Fab was added to the wells and incubated for 1 h at 37° C. After four washes with PBS-Tween 20, strepavidin-alkaline phosphatase (Pierce) was added at a 1:500 dilution and incubated for 1 h at 37° C. The color was developed as described above.

In Vitro Neutralization of HEV with in Vivo Monitoring in Rhesus Monkeys

Rhesus monkeys that were anti-HEV negative (<1:100) in a sensitive ELISA [Tsarev, 1993 #171] were used in this study. Ten monkeys were divided into five groups of two animals each. A 10% stool suspension of the Pakistani HEV strain, SAR-55, was diluted such that each animal would receive 64 monkey infectious doses 50 ($MID_{50}$). This was incubated with either purified Fab or chimpanzee serum. HEV#4, HEV#31 and an irrelevant Fab, HBV#8, were diluted to 1.9 mg ml$^{-1}$ in 10% BSA/PBS. Ten percent solutions of chimpanzee 5835 pre-immune serum and hyper-immune serum were made in 10% BSA/PBS. Virus and antibody were mixed and incubated for 1 h at room temperature, then at 4° C. overnight. The inoculum was divided in half and diluted with 1 ml of ice-cold PBS prior to intravenous inoculation. Serum samples were collected prior to inoculation and for 20 weeks thereafter. Sera were assayed for levels of alanine amino transferase (ALT) with commercially available tests (Metpath Inc.). The anti-HEV ELISA was performed as described elsewhere [Tsarev, 1993]. Seroconversion to HEV was used as the criterion for infection.

Construction of Clones Expressing Truncated SAR-55 ORF2 Proteins

Truncated SAR-55 ORF2 proteins were made by PCR amplification of portions of the HEV ORF2 gene from pHEVORF2 63.2 [Tsarev, 1993]. Truncations from the carboxy-terminal end of the protein were made using the following primers: 5' SAR-55 aa112 (5'-ATGGCGGTCGCTCCGGCCCATGACACCC-3', SEQ ID NO: 38), with one of 3' SAR-55 aa208 (5'-CTATTAAATGGAGATAGCGTAGCCACCAACAGC-3', SEQ ID NO: 39), 3' SAR-55 aa308 (5'-CTATTAGCGGAACTCAAGTTCGAGGGCAAAGTC-3', SEQ ID NO: 40), 3'SAR-55 aa408 (5'-CTATTAAGTCGGCTCGCCATTGGCTGAGACGAC-3', SEQ ID NO: 41), 3' SAR-55 aa508 (5'-CTATTACTGCGCGCCGGTCGCAACATTAACCAA-3', SEQ ID NO: 42), 3' SAR-55 aa578 (5'-CTATTACCGATGCCCAGCGGCATTCTCAACG-3', SEQ ID NO: 43), or 3' SAR-55 aa607 (5'-CTATTATAGCACAGAGTGGGGGGCTAAAACA-3', SEQ ID NO: 44). Amino acids 112 through 607 comprise the 55 kD protein used previously in vaccination studies [Tsarev, 1994; Tsarev, 1997]. Amino acids 112 through 578 represent a 53 kD protein, which readily formed virus-like particles, when examined under the electron microscope. The 5' SAR-55 aa112 primer was phosphorylated with T4 polynucleotide kinase prior to PCR amplification, and the products were cloned into the mammalian e4xpression vector, pCR 3.1 (Unidirectional TA cloning kit, Invitrogen).

In Vitro Transcription and Translation, and Radioimmunoprecipitation of $^{35}$S-labeled Truncated SAR-55 ORF2 Proteins In vitro transcription and translation of the truncated SAR-55 ORF2 clones aa208 to aa607 were carried out according to the manufacturer's protocol (T7 TNT in vitro transcription/translation, Promega) using $^{35}$S-methionine (Redivue, Amersham) as the radiolabel. The six truncated ORF2 products were visualized on a 10–20% PAGE gel followed by autoradiography, then pooled. Five microliters of pooled truncated products were mixed with 1 μl of antibody and 5 μl of 2× native RIPA buffer [0.5 M NaCl, 5% glycerol, 0.2 M Tris-HCl (pH 8.0), 1.0% Tween-20, 2 mM EDTA] and incubated with rocking overnight at 4° C. For chimpanzee 1441 pre- and post-immune sera, precipitations were performed with the addition of recombinant protein G-coupled agarose beads (Gibco), and incubation with rocking on ice for 1 h. For HEV#4, HEV#31 and HBV#8 Fab, a 1 μl of goat anti-human IgG (F(ab')$_2$-specific) was used in addition to protein G-coupled agarose beads. The beads were pelleted, washed three times in 1× RIPA buffer and once with distilled, deionized $H_2O$ (dd$H_2O$). Samples were then resuspended in 15 μL 2× Laemelli buffer and incubated for 10 min. at 95° C. prior to loading on to a 10–20% PAGE gel (Novex). After 1 h at 126 V, the gel was fixed in a solution of 10% acetone and 10% methanol for 20 min., washed twice in d$H_2O$, then incubated in Amplify solution (Amersham) for 20 min. After drying, the gel was exposed to X-ray film at −70° C.

Results

Isolation and Characterization of HEV ORF 2-specific Fabs

Chimpanzee 1441 had been previously experimentally infected with the HEV SAR-55 (Pakistan strain, Asian/African genotype). Prior to the bone marrow aspiration, the chimpanzee was immunized once with baculovirus-expressed SAR-55 ORF 2 (55 kD) protein. Total RNA was extracted from bone marrow lymphocytes. Messenger RNA was reverse transcribed using an oligo (dT) primer to generate cDNA. Amplification of the cDNA was carried out by PCR using both κ-chain and γ1-chain primers specific for the human antibody genes. The amplified κ- and γ1-chain genes were purified and cloned into the phage display vector, pComb3H. The resultant Fab phage library was then selected against baculovirus-expressed SAR-55 ORF 2 protein. After four rounds of panning, the library DNA was isolated and the phage display vector modified by restriction enzyme digestion to allow for soluble Fab expression in *E. coli*. An ELISA was used to determine the specificity of the Fabs using the HEV ORF 2 protein and a panel of unrelated protein antigens. Of the 144 clones screened, seven were SAR-55 ORF2-specific.

As the restriction enzyme Bst N1 cuts frequently in the human γ1-heavy chain [Marks, 1991], the resulting restriction patterns can be used to predict the presence of different heavy chain sequences amongst the Fab clones. There were two distinct Bst N1 restriction patterns observed, one represented by five clones of HEV#4, and the other by two clones of HEV#31 (FIG. 1a).

Sequence analysis of the seven Fab clones confirmed the results of the Bst N1 digest above. There were two distinct γ1-heavy chains; one was represented by HEV#4 clones and the other by HEV#31 clones. The two γ1-chains varied markedly in all three complementarity-determining regions (CDR; FIG. 1b). The κ-light chain sequences were also divergent (FIG. 7).

The specific germ-line origin of the two monoclonal antibodies was assessed by conducting a sequence similarity search of all the known human immunoglobulin genes. The two γ1-heavy chain sequences exhibited the most homology with the human VH3 family of germ line segments (Table 1). HEV#4 was most closely related to DA-8 [Cook, 1994] VH gene segment, with 89.4% overall homology and 92% excluding CDR1 and CDR2. HEV#31 was most closely related to DP-47 [Tomlinson, 1992] VH gene segment, with 88.5% overall homology and 91.7% excluding CDR1 and CDR2. The κ-light chain sequences exhibited the most homology with the human Vκ1 family of germ line segments.

The affinities of the monoclonal antibodies were determined using BIAcore™. Association and dissociation kinetics were measured for both HEV#4 and HEV#31 binding to SAR-55 ORF2 protein (Table 2). Both monoclonal antibodies had high equilibrium dissociation constants ($K_d$), 1.7 nM for HEV#4 and 4.5 nM for HEV#31.

TABLE 1

| Fab | $V_H$ family | $V_H$ segment | D segment | $J_H$ segment | $V_\kappa$ family | $V_\kappa$ segment | $J_\kappa$ segment |
|---|---|---|---|---|---|---|---|
| HEV #4 | VH3 | DA-8 | ND* | JH4b | Vκ1 | HK137 | Jκ1 |
| HEV #31 | VH3 | DP-47 | ND* | JH4b | Vκ1 | DPK9 | Jκ4 |

*ND not determined due to lack of an identifiable homologue.

TABLE 2

| MAb | $K_d$ (nM) | $k_a$ ($10^5$ $M^{-1}$ $s^{-1}$) | $k_d$ ($10^{-4}$ $s^{-1}$) |
|---|---|---|---|
| HEV#4 | 1.7 | 1.2 | 3.5 |
| HEV#31 | 4.5 | 0.54 | 4.9 |

Figure 2:
FIG. 2 shows a Western blot of HEV ORF2 protein (55 kD) immunoblotted with chimpanzee 1441 post-immune serum (lane A), HEV#4 (lane B), and HEV#31 (lane C), respectively. The positions of molecular weight markers are shown on the left side of the blot.

A Western blot was performed to determine the nature of the epitopes recognized by the two monoclonal antibodies (i.e. linear or conformational epitopes). HEV#4 and HEV#31 both recognized reduced, denatured HEV ORF2 protein (FIG. 2), suggesting that they are both directed to linear epitopes on the virus capsid.

An indirect competition assay was performed to determine whether the two monoclonal antibodies recognized similar or overlapping epitopes on the HEV capsid (Table 3). Unlabeled HEV#4 blocked the binding of biotinylated HEV#31 to the SAR-55 ORF2 protein, and vice versa. Therefore, HEV#4 and HEV#31 recognized similar or overlapping epitopes on the SAR-55 ORF2 protein.

TABLE 3

| | Biotinylated Fab | |
|---|---|---|
| Unlabeled Fab | HEV#4 | HEV#31 |
| HEV#4 | 63* | 66 |
| HEV#31 | 72 | 81 |

*percent inhibition of binding

Radioimmunoprecipitation assays were carried out to determine the location of the epitopes on the HEV capsid. Purified HEV#4 and HEV#31 were incubated at 4° C. overnight with a pool of six $^{35}$S-labeled C-terminal truncated ORF2 translation products, shown schematically in FIG. 3a. Both monoclonal antibodies precipitated SAR-55 aa607 (FIG. 3b), corresponding to the 55 kD panning antigen. However, the shorter polypeptides were not precipitated to any significant degree. Chimpanzee 1441 immune serum precipitated SAR-55 aa308 to SAR-55 aa607, whilst the pre-immune serum did not react with any. SAR-55 aa208 was too poorly radiolabeled to determine whether it was precipitated. HAV#6, an HAV-specific monoclonal antibody, did not precipitate any of the ORF2 truncations, nor did the secondary antibody alone or protein G alone (FIG. 3b).

Figure 4:
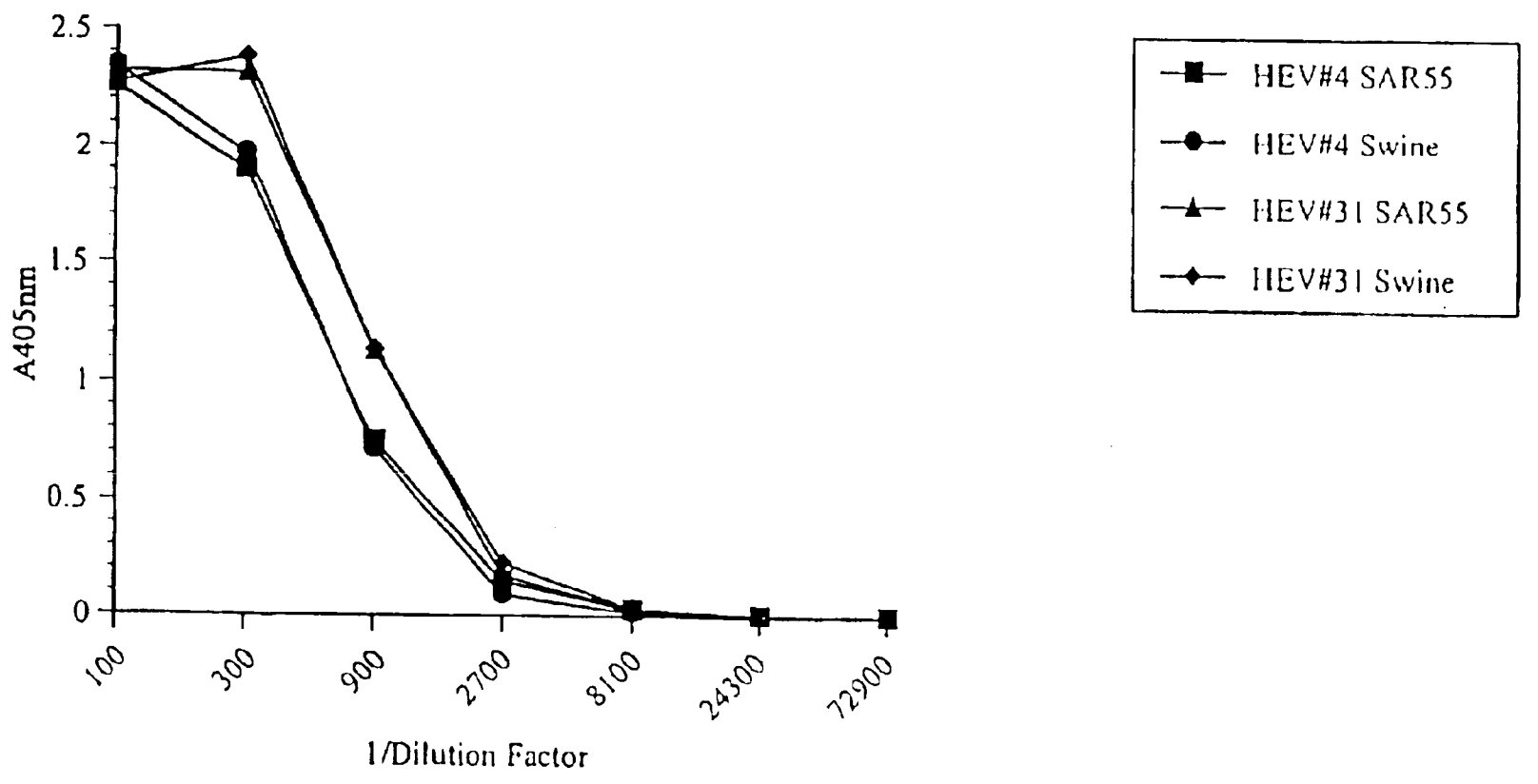

Currently, only one serotype of HEV is known. However, there are a number of divergent strains of HEV based on nucleotide and amino acid sequences. Two of the most divergent strains of HEV are Pakistan (SAR-55) and swine HEV. The two Fabs were tested by ELISA for cross-reactivity with the swine HEV ORF2 protein. Titration curves for HEV#4 and HEV#31 were identical for the heterologous swine and homologous SAR-55 ORF2 proteins (FIG. 4).

In vitro Neutralization of HEV with in vivo Monitoring in Rhesus Monkeys

Figure 5:
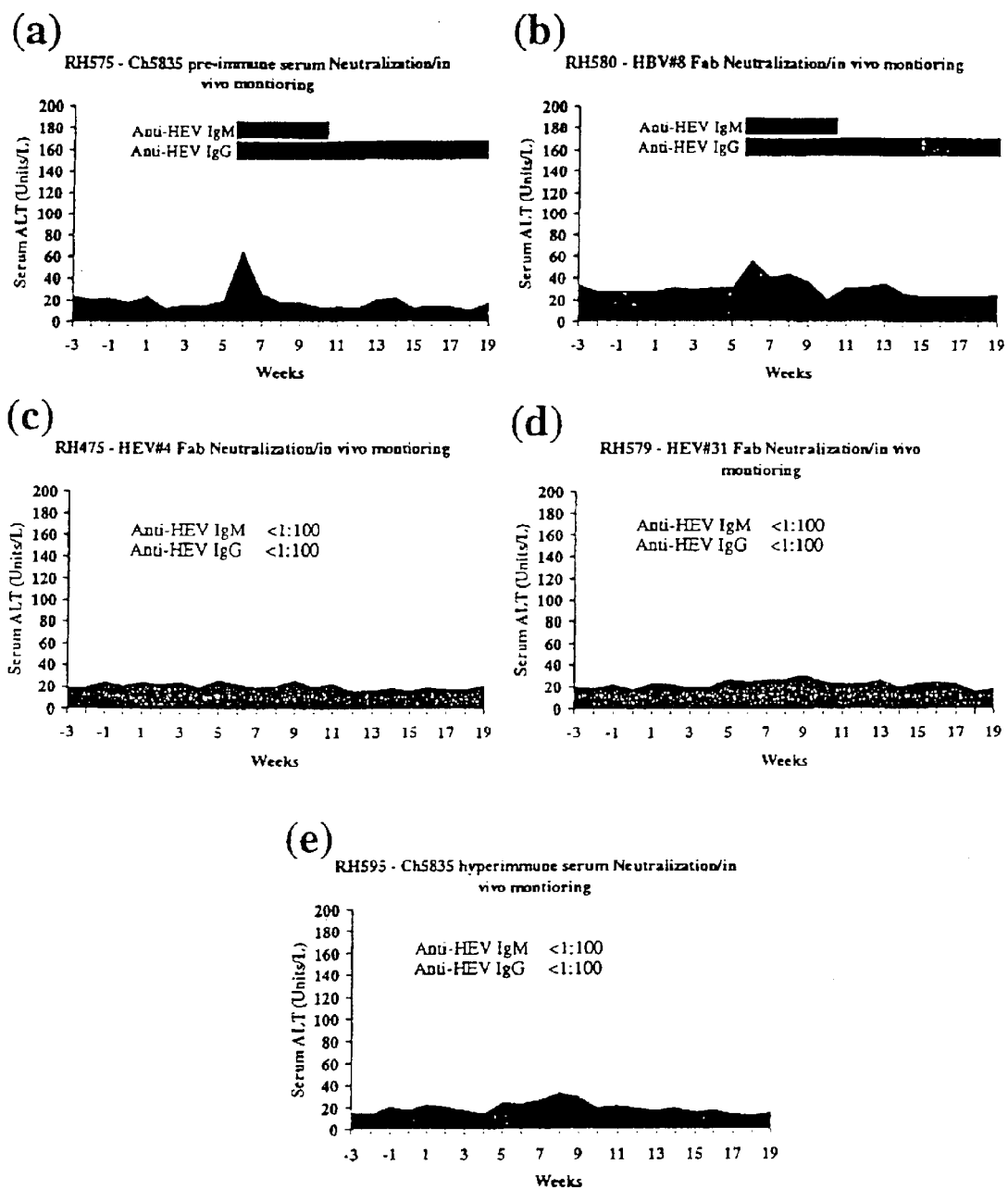
FIG. 5 shows in vitro neutralization of HEV with in vivo monitoring in rhesus monkeys inoculated with HEV treated with (a) chimpanzee 5835 pre-immune serum, (b) HBV#8 Fab, (c) HEV#4, (d) HEV#31, and (e) chimpanzee 5835 hyper-immune serum.

Sixty four 50% monkey infectious doses ($MID_{50}$) of HEV strain SAR-55 were incubated with HEV#4, HEV#31, or an irrelevant Fab HBV#8, at 1.9 mg ml$^{-1}$, or with a 10% solution of either chimpanzee 5835 pre- or hyper-immune serum prior to inoculation into rhesus monkeys. Inoculations were performed in duplicate. After intravenous inoculation, the monkeys were followed for 20 weeks for biochemical evidence of hepatitis (serum ALT) and for seroconversion to HEV antigens by ELISA. All the monkeys that received HEV incubated either with chimpanzee 5835 pre-immune serum or HBV#8 were infected and developed hepatitis, as evidenced by a rise in ALT levels and seroconversion to HEV ORF2 protein (examples shown in FIG. 5a, b). In contrast, all monkeys receiving HEV incubated with HEV#4, HEV#31 or chimpanzee 5835 hyper-immune serum had normal ALT levels and did not seroconvert to HEV ORF2 protein (examples shown in FIG. 5c–e).

Antibodies EBL#2 and EBL#89 (listed in FIG. 8) were tested for their ability to neutralize HEV (SAR-55 strain) by mixing virus and antibody in vitro as described above and monitoring for residual infectivity by intravenous inoculation of rhesus monkeys. Antibodies EBL#2 and EBL#89 were selected because they did not inhibit binding of each other to HEV ORF2 protein. Nor did they inhibit binding of the two neutralizing MAbs (HEV#4 and HEV#31) to the HEV ORF2 protein (FIG. 9). Therefore, each was directed to a unique non-overlapping epitope on the HEV ORF2 protein. Panel (A) shows the serum ALT profile over 15 weeks of follow-up for one of the two animals receiving HEV (SAR-55 strain) mixed with EBL#2. The rise in ALT at week 6 and subsequent seroconversion to anti-HEV (IgM and IgG) indicated that this antibody did not neutralize HEV (i.e. the epitope it recognizes is a non-neutralization epitope). Panel (B) shows the serum ALT profile over 15 weeks of follow-up for one of the two animals receiving HEV (SAR-55 strain) mixed with EBL#89. The rise in ALT at week 10 and seroconversion to anti-HEV (IgM and IgG) indicated that this antibody did not neutralize HEV (i.e. the epitope it recognizes is a non-neutralization epitope). Panel (C) is a positive control hyper-immune serum which does neutralize the SAR-55 inoculum.

Figure 10:
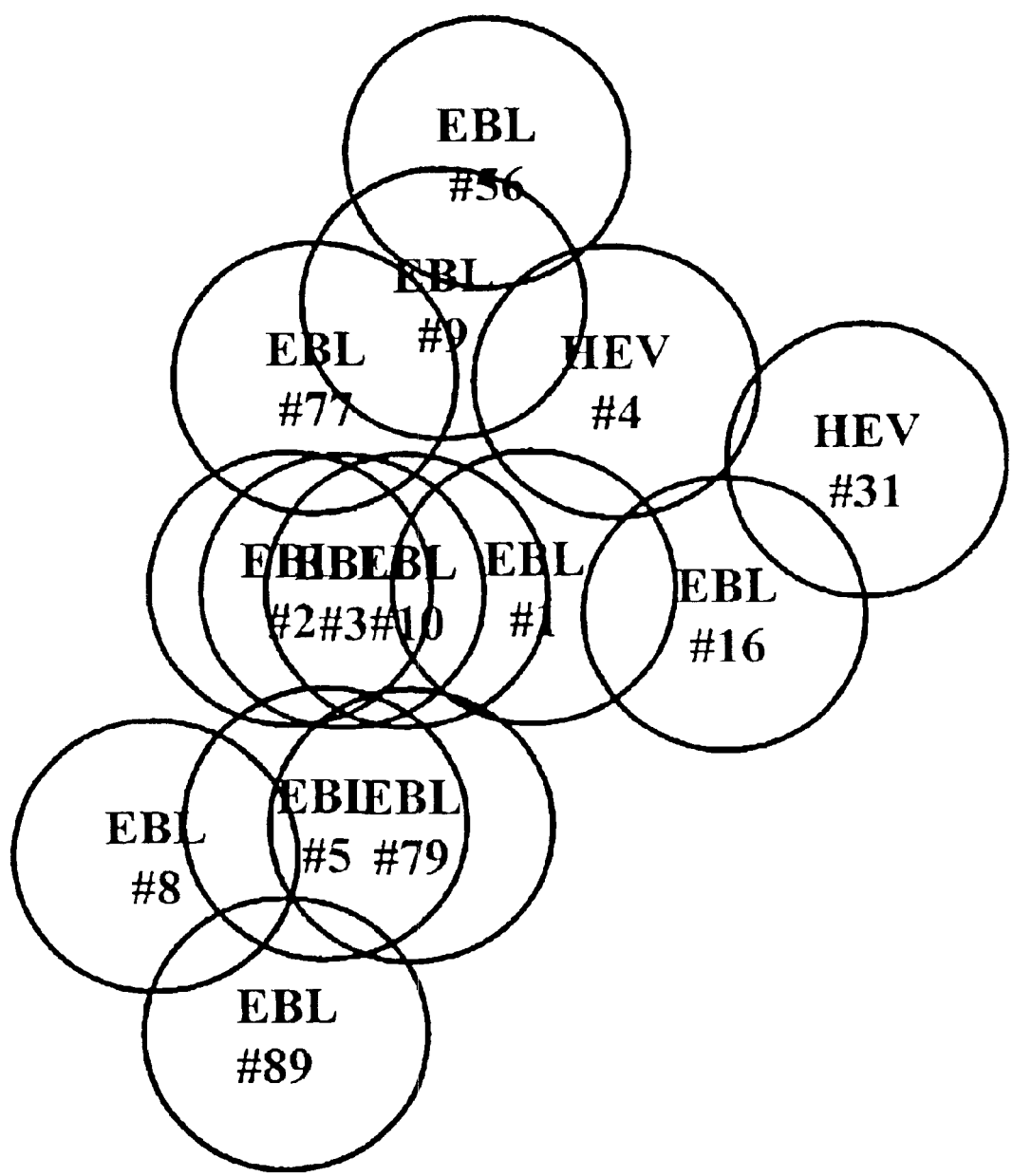
FIG. 10 shows the topography of the epitopes recognized by the antibodies listed in FIG. 8. Where two circles overlap there is greater than 50% inhibition of binding between the antibody pair.

The MAbs listed in FIG. 8 were used in pair-wise competition ELISAs to determine the topography of the epitopes recognized by these antibodies. The data is summarized in FIG. 10. Where two circles overlap there is >50% inhibition of binding between the antibody pair. However, the degree of overlap does not represent the percentage inhibition of binding between each antibody pair. The data indicate that all the MAbs are directed to a single antigenic site on the HEV ORF2 protein. That antigenic site comprises overlapping and non-overlapping epitopes.

Figure 11:
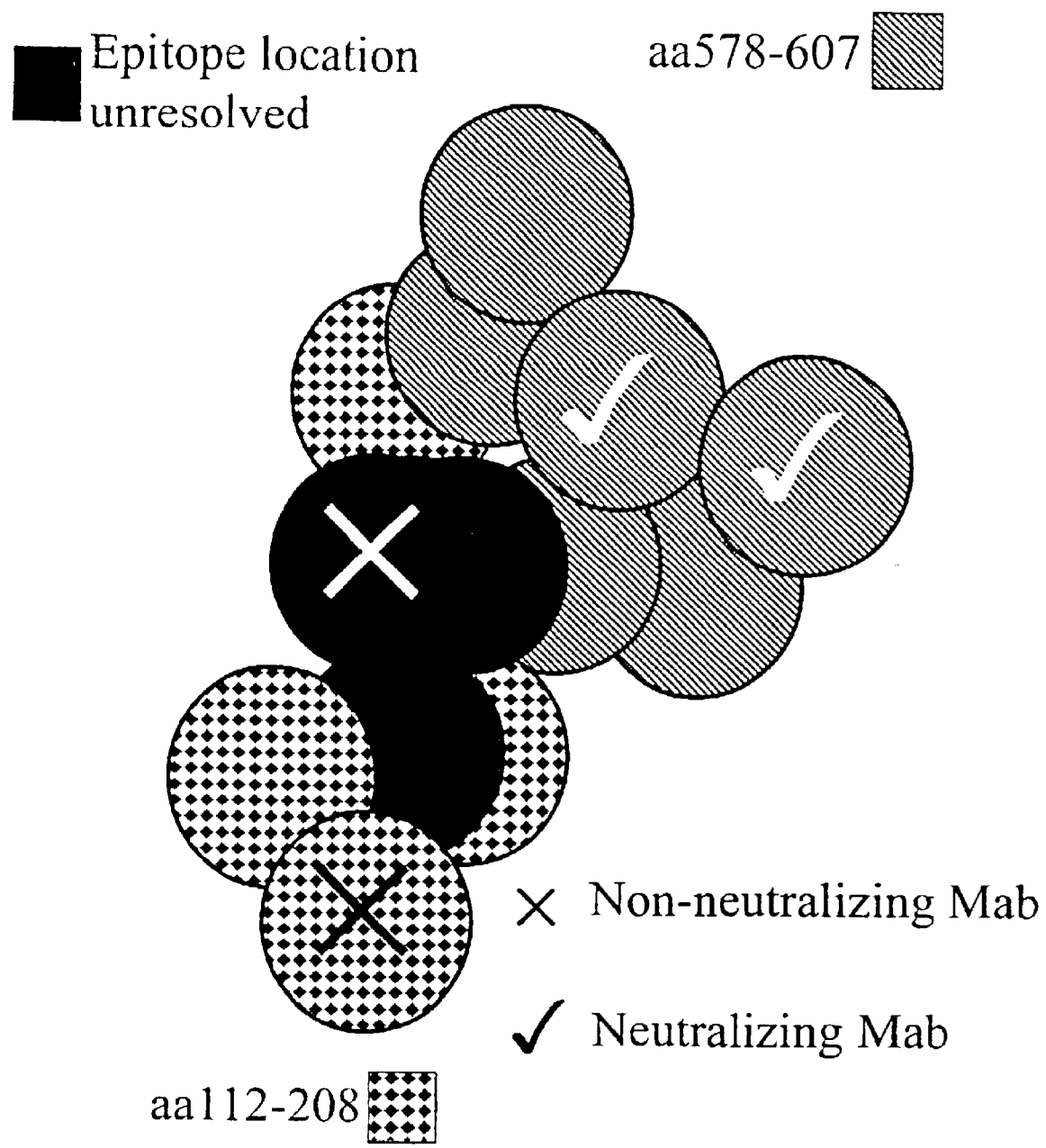
FIG. 11 shows a topographical map of the HEV ORF2 antigenic site overlaid with epitope recognition data from radioimmunoprecipitation studies. The locations of the neutralization and non-neutralization epitopes on the topographical map of the HEV ORF2 antigenic site are indicated with a "✓" and a "X", respectively.

Both C-terminally and N-terminally truncated forms of the SAR-55 ORF2 55 kD protein (amino acids 112–607) were constructed in order to map the location of the epitopes on the ORF2 protein recognized by the panel of MAbs listed in Table 4 and FIG. 8. FIG. 11 shows the data from radioimmunoprecipitation studies overlaid on top of the topographical map of the HEV ORF2 antigenic site. Analysis of the data indicated that four MAbs recognized epitopes located at the N-terminal portion of the HEV ORF2 55 kD protein (between amino acids 112 and 208). Six MAbs mapped to the C-terminal portion of the 55 kD protein (between amino acids 578 and 607). This region contains the neutralization epitopes. Four MAbs are unresolved by this study. Three MAbs, which could not be mapped by pair-wise competition assays, also recognized epitopes in the C-terminal portion of the HEV ORF2 55 kD protein. These results are summarized in Table 4. FIG. 11 depicts the location of the neutralization and non-neutralization epitopes on the ORF2 protein.

TABLE 4

| Mab | Epitope Location | Activity |
|---|---|---|
| HEV#4 | 578–607 | Neutralizing |
| HEV#31 | 578–607 | Neutralizing |
| EBL#1 | 578–607 | |
| EBL#2 | unresolved | Non-neutralizing |
| EBL#3 | unresolved | |
| EBL#4 | 578–607 | |
| EBL#5 | unresolved | |
| EBL#8 | 112–208 | |
| EBL#9 | 578–607 | |
| EBL#10 | unresolved | |
| EBL#16 | 578–607 | |
| EBL#33 | 578–607 | |

TABLE 4-continued

| Mab | Epitope Location | Activity |
|---|---|---|
| EBL#53 | 578–607 | |
| EBL#56 | 578–607 | |
| EBL#77 | 112–208 | |
| EBL#79 | 112–208 | |
| EBL#89 | 112–208 | Non-neutralizing |

There are at least three genotypes of HEV: genotype 1 comprising strains from Asia and Africa, genotype 2 comprising the Mexican strain, and genotype 3 comprising the human US strains and the swine HEV, Meng strain. To determine whether this panel of MAbs could recognize ORF2 proteins from other genotypes, we initially performed a qualitative ELISA. All of the MAbs tested (16 of 17) recognized the ORF2 protein from the homologous strain SAR-55, and also recognized the ORF2 protein from the genotype 3 swine HEV Meng strain (data not shown). Subsequently a quantitative measurement of antibody binding was undertaken. The affinities of these MAbs for the SAR-55 and Meng ORF2 proteins were determined. For fifteen of sixteen MAbs, the affinity values were comparable indicating conservation of epitopes between the two strains. However, one MAb, EBL#16 had a >1000-fold reduction in affinity for the Meng strain ORF2 protein compared to that for the SAR-55 ORF2 protein, thus indicating that an amino acid(s) substitution in or near this epitope is responsible for the reduction in affinity. Since EBL#16 precipitated C-607 only, it is likely that the epitope recognized lies between about aa578 and about aa607 of the ORF2 protein. A comparison of the amino acid sequences in this region for a number of HEV isolates is shown in FIG. 6 with SAR-55 and Meng strains highlighted. There are only 5 amino acid differences between the two strains. Hence it is likely that one or more of these amino acid changes is responsible for the reduction in affinity for the Meng ORF2 protein. Thus, it is possible to make diagnostic assays that distinguish between infection with swine HEV and some human HEV strains.

It is also interesting to note that the epitopes recognized by the two neutralizing MAbs HEV#4 and HEV#31 are conserved between the two divergent HEV strains. If these neutralization sites are conserved in other strains of HEV then these antibodies would be broadly effective in passive immunoprophylaxis and immunotherapy.

The affinities of all of the MAbs for both SAR-55 ORF2 protein (homologous strain) and the swine HEV, Meng strain (heterologous strain) were determined by competition inhibition ELISA. The concentration of free ORF2 protein required to inhibit antibody binding by 50% is equivalent to the equilibrium dissociation constant ($K_d$). The $K_d$ values for the Fab are summarized in Table 5.

TABLE 5

| | Kd (nM) | |
|---|---|---|
| MAb | SAR-55 ORF2 | Swine ORF2 |
| HEV#4 | 3.3 | 7.0 |
| HEV#31 | 0.8 | 1.3 |
| EBL#1 | 15.0 | 22.5 |
| EBL#2 | 2.0 | 4.0 |
| EBL#3 | 3.0 | 4.8 |
| EBL#4 | ND[#] | ND[#] |

TABLE 5-continued

| | Kd (nM) | |
| MAb | SAR-55 ORF2 | Swine ORF2 |
| --- | --- | --- |
| EBL#5 | 1.1 | 3.0 |
| EBL#8 | 0.7 | 1.8 |
| EBL#9 | 45.0 | 35.0 |
| EBL#10 | 2.0 | 3.0 |
| EBL#16 | 1.3 | >1000* |
| EBL#33 | >1000* | >1000* |
| ERL#53 | 400.0 | ≧1000* |
| EBL#56 | 48.0 | 45.0 |
| EBL#77 | 1.9 | 4.0 |
| EBL#79 | 4.0 | 8.5 |
| EBL#89 | 2.0 | 3.3 |

ND indicates not determined;
*1000 nM is the lower limit of detection for the assay used.

Discussion

Antibodies to a wide range of viral pathogens have been isolated using combinatorial antibody libraries displayed on the surface of filamentous phage particles. In most studies, human donors infected with specific viral pathogens have been used as the source of bone marrow cells or peripheral blood lymphocytes for the construction of these libraries. In some studies, "naïve" libraries have been constructed using uninfected donors [Marks, 1991]. In the present invention, a chimpanzee previously infected with specific viral pathogens was used as a source of bone marrow lymphocytes for the construction of a phage display library. The advantages of using a chimpanzee as a donor for repertoire cloning are two-fold: first, the chimpanzee can be infected by many of the important human viral pathogens with limited host range, e.g. HIV-1, HCV, HBV, and RSV; second, as the chimpanzee is the primate most closely related to humans, chimpanzee antibodies could theoretically be used directly in the immune prophylactic treatment of human diseases. A number of studies have addressed the possibility of using primate reagents in human prophylaxis and therapy by examining the reverse situation, i.e. introduction of human immune components into primates [Logdberg, 1994; Ehrlich, 1988; Ehrlich, 1988; Ehrlich, 1987; Ehrlich, 1990]. The data from those studies show that little immunogenicity is seen when human immune components are introduced into chimpanzees compared to other primates.

The cDNA phage display library described herein is a potential repertoire for antibodies to the five recognized hepatitis-causing viruses, HAV, HBV, HCV, HDV and HEV. In the initial study, two HEV-specific monoclonal antibodies directed to the ORF2 protein were identified. The γ1-heavy chains of those two monoclonal antibodies share a high degree of homology (89.4% for HEV#4 and 88.5% for HEV#31) at the nucleotide level with two different γ1-heavy chains from the human VH3 gene family. The degree of homology between the chimpanzee and human γ-chain genes was similar to that of the only other chimpanzee antibody characterized to date. For an anti-HIV gp160 monoclonal antibody, there was 92% homology with its nearest human germ line equivalent. This was estimated to be more homologous than the two most distantly related human VH gene families [Vijh-Warrier, 1995]. Such close sequence homology between chimpanzee and human antibody genes suggests that chimpanzee antibodies could be useful in human immunotherapy without modification ("humanization"). However, as with human monoclonal antibodies, each monoclonal antibody would require testing for immunogenicity in humans.

HEV#4 and HEV#31 have high affinities for the ORF2 protein from HEV strain SAR-55, with $K_d$ values in the nanomolar range. These values were comparable to $K_d$ values determined for other neutralizing Fabs to other viruses, e.g. influenza A virus [Schofield, 1996], HIV-1 [Burton, 1994], and murine hepatitis virus [Lamarre, 1995]. In Western blot, both HEV#4 and HEV#31 recognized reduced, denatured ORF2 suggesting that they are directed to linear rather than conformational epitopes on the ORF2 protein. In indirect competition assays, HEV#4 and HEV#31 recognized similar or overlapping epitopes on the ORF2 protein since each Fab inhibited the other from binding. The location of this epitope or epitopes was determined by radioimmunoprecipitation of C-terminally truncated SAR-55 ORF2 proteins. HEV#4 and HEV#31 strongly precipitated only the construct corresponding to aa112–607 (55 kD protein), suggesting that the majority of the epitope(s) lies between aa578 and aa607 on the ORF2 protein. This epitope(s) forms part of the antigenic region 6 designated by Khudyakov et al. [Khudyakov, 1999]. The weakly precipitated ORF2 truncation products aa112 to aa308, aa112 to aa408, aa112 to aa508 and aa112 to aa578 probably represent non-specific protein-protein interactions. The amino acid sequence between aa578 and aa607 is relatively conserved amongst HEV isolates (FIG. 6), with the Mexican strain having the most amino acid changes, 5 out of 30. Reactivity of the two monoclonal antibodies with recombinant ORF2 protein from a highly divergent heterologous strain, swine HEV, was determined by ELISA. Both monoclonal antibodies had similar titration curves with the SAR-55 ORF2 and swine ORF2 proteins. Since this region is relatively well conserved, it is conceivable that the epitope(s) recognized by HEV#4 and HEV#31 are likely to be conserved amongst many of the different HEV isolates. Currently, cloning of the ORF2 from the Mexico strain is being attempted in order to determine if the epitope(s) is conserved in this region of ORF2 from the most divergent strain.

Neutralization of the SAR-55 strain of HEV by monoclonal antibodies HEV#4 and HEV#31 was determined by intravenous challenge of rhesus monkeys with 64 $MID_{50}$ after incubation of the virus with the two monoclonal antibodies. All the animals receiving HEV incubated with either HEV#4 or HEV#31 did not seroconvert to anti-HEV, nor was any rise in serum ALT levels detected. In contrast, all control animals were infected with HEV since they seroconverted to anti-HEV, and also had mild ALT elevations. Therefore, both HEV#4 and HEV#31 neutralized HEV. Furthermore, since the Fabs are monovalent, neutralization of HEV was not due to a reduction in the infectious dose given to the monkeys due to the aggregation of virus particles. Neutralization of HEV was caused by the binding of the monoclonal antibodies alone, since the Fab fragments which lack an Fc region would not be able to neutralize the virus by an Fc-mediated function, such as antibody-dependent cell mediated cytotoxicity.

Currently, here is no vaccine available for the prevention of HEV infection. Therefore, there is a need for anti-HEV immunoglobulins which can be used for protecting individuals at high risk from HEV infection. Since currently such therapies are very expensive, economically viable and renewable sources of potent IgGs would be very beneficial. At the present, the production of antibodies generated from stably transfected cell lines is still prohibitively expensive. However, new techniques such as the expression of whole IgG molecules in plants [Ma, 1998] may make these antibodies cheaper to produce, and economically viable. In addition to being a potential source of antibodies for passive immunoprophylaxis, this cDNA library described herein could also provide a repository of antibodies which may be helpful in elucidating the type of antibodies successful vaccines should be stimulating.

References

1. Arankalle, V. A., Goverdhan, M. K., Banerjee, K. 1994. Antibodies against hepatitis E virus in old world monkeys. Journal of Viral Hepatitis. 1:125–129.
2. Aye, T. T., T. Uchida, X. Z. Ma, F. Iida, T. Shikata, H. Zhuang, and K. M. Win. 1992. Complete nucleotide sequence of a hepatitis E virus isolated from the Xinjiang epidemic (1986–1988) of China. Nucleic Acids Res. 20:3512.
3. Barbas, C. F. d., A. S. Kang, R. A. Lerner, and S. J. Benkovic. 1991. Assembly of combinatorial antibody libraries on phage surfaces: the gene III site. Proc Natl Acad Sci U S A. 88:7978–82.
4. Bender, E., G. R. Pilkington, and D. R. Burton. 1994. Human monoclonal Fab fragments from a combinatorial library prepared from an individual with a low serum titer to a virus. Hum Antibodies Hybridomas. 5:3–8.
5. Bender, E., J. M. Woof, J. D. Atkin, M. D. Barker, C. R Bebbington, and D. R. Burton. 1993. Recombinant human antibodies: linkage of an Fab fragment from a combinatorial library to an Fc fragment for expression in mammalian cell culture. Hum Antibodies Hybridomas. 4:74–9.
6. Bi, S. L., M. A. Purdy, K. A. McCaustland, H. S. Margolis, and D. W. Bradley. 1993. The sequence of hepatitis E virus isolated directly from a single source during an outbreak in China [published erratum appears in Virus Res 1994 July; 33(1):98]. Virus Res. 28:233–47.
7. Burton, D. R., and C. F. Barbas, 3rd. 1994. Human antibodies from combinatorial libraries. Adv Immunol. 57:191–280.
8. Burton, D. R., C. F. d. Barbas, M. A. Persson, S. Koenig, R. M. Chanock, and R. A. Lerner. 1991. A large array of human monoclonal antibodies to type 1 human immunodeficiency virus from combinatorial libraries of asymptomatic seropositive individuals. Proc Natl Acad Sci U S A. 88:10134–7.
9. Burton, D. R., J. Pyati, R. Koduri, S. J. Sharp, G. B. Thornton, P. W. Parren, L. S. Sawyer, R. M. Hendry, N. Dunlop, P. L. Nara, and et al. 1994. Efficient neutralization of primary isolates of HIV-1 by a recombinant human monoclonal antibody. Science. 266:1024–7.
10. Clayson, E. T., B. L. Innis, K. S. Myint, S. Narupiti, D. W. Vaughn, S. Giri, P. Ranabhat, and M. P. Shrestha. 1995. Detection of hepatitis E virus infections among domestic swine in the Kathmandu Valley of Nepal. Am J Trop Med Hyg. 53:228–32.
11. Cook, G. P., and I. M. Tomlinson. 1995. The human immunoglobulin VH repertoire. Immunol Today. 16:237–42.
12. Cook, G. P., I. M. Tomlinson, G. Walter, H. Riethman, N. P. Carter, L. Buluwela, G. Winter, and T. H. Rabbitts. 1994. A map of the human immunoglobulin VH locus completed by analysis of the telomeric region of chromosome 14q. Nat Genet. 7:162–8.
13. Crowe, J. E., Jr., B. R. Murphy, R. M. Chanock, R. A. Williamson, C. F. Barbas, 3rd, and D. R. Burton. 1994. Recombinant human respiratory syncytial virus (RSV) monoclonal antibody Fab is effective therapeutically when introduced directly into the lungs of RSV-infected mice. Proc Natl Acad Sci U S A. 91:1386–90.
14. de Kruif, J., A. R. van der Vuurst de Vries, L. Cilenti, E. Boel, W. van Ewijk, and T. Logtenberg. 1996. New perspectives on recombinant human antibodies. Immunol Today. 17:453–5.
15. Ditzel, H. J., P. W. Parren, J. M. Binley, J. Sodroski, J. P. Moore, C. F. Barbas, 3rd, and D. R. Burton. 1997. Mapping the protein surface of human immunodeficiency virus type 1 gp120 using human monoclonal antibodies from phage display libraries. J Mol Biol. 267:684–95.
16. Donati, M. C., Fagan, E. A., and Harrison, T. J. 1997. Sequence analysis of full length HEV clones derived directly from human liver in fulminant hepatitis E., p. 313–316. In M. Rizzetto, Purcell, R. H., Gerin, J. L., and Verme, G. (ed.), Viral Hepatitis and Liver Disease. Edizioni Minervva Medica, Torino.
17. Ehrlich, P. H., K. E. Harfeldt, J. C. Justice, Z. A. Moustafa, and L. Ostberg. 1987. Rhesus monkey responses to multiple injections of human monoclonal antibodies. Hybridoma. 6:151–60.
18. Ehrlich, P. H., Z. A. Moustafa, K. E. Harfeldt, C. Isaacson, and L. Ostberg. 1990. Potential of primate monoclonal antibodies to substitute for human antibodies: nucleotide sequence of chimpanzee Fab fragments. Hum Antibodies Hybridomas. 1:23–6.
19. Ehrlich, P. H., Z. A. Moustafa, J. C. Justice, K. E. Harfeldt, I. K. Gadi, L. J. Sciorra, F. P. Uhl, C. Isaacson, and L. Ostberg. 1988. Human and primate monoclonal antibodies for in vivo therapy. Clin Chem. 34:1681–8.
20. Ehrlich, P. H., Z. A. Moustafa, J. C. Justice, K. E. Harfeldt, and L. Ostberg. 1988. Further characterization of the fate of human monoclonal antibodies in rhesus monkeys. Hybridoma. 7:385–95.
21. Geoffroy, F., R. Sodoyer, and L. Aujame. 1994. A new phage display system to construct multicombinatorial libraries of very large antibody repertoires. Gene. 151:109–13.
22. Glamann, J., D. R. Burton, P. W. Parren, H. J. Ditzel, K. A. Kent, C. Arnold, D. Montefiori, and V. M. Hirsch. 1998. Simian immunodeficiency virus (SIV) envelope-specific Fabs with high-level homologous neutralizing activity: recovery from a long-term-nonprogressor SIV-infected macaque. J Virol. 72:585–92.
23. Huang, C. C., D. Nguyen, J. Fernandez, K. Y. Yun, K. E. Fry, D. W. Bradley, A. W. Tam, and G. R. Reyes. 1992. Molecular cloning and sequencing of the Mexico isolate of hepatitis E virus (HEV). Virology. 191:550–8.
24. Joshi, Y. K., S. Babu, S. Sarin, B. N. Tandon, B. M. Gandhi, and V. C. Chaturvedi. 1985. Immunoprophylaxis of epidemic non-A non-B hepatitis. Indian J Med Res. 81:18–9.
25. Kabrane-Lazizi, Y., X. J. Meng, R. H. Purcell, and S. U. Emerson. 1999. Evidence that the genomic RNA of hepatitis E virus is capped. J Virol. 73:8848–50.
26. Karetnyi, V., D. I. Dzhumalieva, R. K. Usmanov, I. P. Titova, I. Litvak Ia, and M. S. Balaian. 1993. [The possible involvement of rodents in the spread of viral hepatitis E]. Zh Mikrobiol Epidemiol Immunobiol:52–6.
27. Khudyakov, Y. E., E. N. Lopareva, D. L. Jue, T. K. Crews, S. P. Thyagarajan, and H. A. Fields. 1999. Antigenic domains of the open reading frame 2-encoded protein of hepatitis E virus. J Clin Microbiol. 37:2863–71.
28. Khuroo, M. S., and M. Y. Dar. 1992. Hepatitis E: evidence for person-to-person transmission and inability of low dose immune serum globulin from an Indian source to prevent it [see comments]. Indian J Gastroenterol. 11:113–6.
29. Khuroo, M. S., M. R. Teli, S. Skidmore, M. A. Sofi, and M. I. Khuroo. 1981. Incidence and severity of viral hepatitis in pregnancy. Am J Med. 70:252–5.

30. Laemelli, E. K. 1970. Cleavage of structural proteins during the assembly of the head of bacteriophage T4. Nature. 227:680–685.
31. Lamarre, A., and P. J. Talbot. 1995. Protection from lethal coronavirus infection by immunoglobulin fragments. J Immunol. 154:3975–84.
32. Logdberg, L., E. Kaplan, M. Drelich, E. Harfeldt, H. Gunn, P. Ehrlich, D. Dottavio, P. Lake, and L. Ostberg. 1994. Primate antibodies to components of the human immune system. J Med Primatol. 23:285–97.
33. Ma, J. K., B. Y. Hikmat, K. Wycoff, N. D. Vine, D. Chargelegue, L. Yu, M. B. Hein, and T. Lehner. 1998. Characterization of a recombinant plant monoclonal secretory antibody and preventive immunotherapy in humans [see comments]. Nat Med. 4:601–6.
34. Marks, J. D., H. R. Hoogenboom, T. P. Bonnert, J. McCafferty, A. D. Griffiths, and G. Winter. 1991. By-passing immunization. Human antibodies from V-gene libraries displayed on phage. J Mol Biol. 222:581–97.
35. Mast, E. E., Alter, M. J. 1993. Epidemiology of viral hepatitis: an overview. Seminars in Virology. 4:273–283.
36. Mast, E. E., Kuramoto, P. O., Favorov M. O., Schoening, V. R., Burkholder, B. T., Shapiro, C. N., Holland, P. V. 1997. Prevelance of and risk factors for antibody to hepatitis E virus seroreactivity among blood donors in northern California. Journal of Infectious Diseases. 176:34–40.
37. Meng, X. J., Purcell, R. H., Halbur, P. G., Lehman, J. R., Webb, D. M., Tsareva, T. S., Haynes, J. S., Thacker, B. J., Emerson, S. U. 1997. A novel virus in swine is closely related to the human hepatitis E virus. PNAS. 94:9860–9865.
38. Ogata, N., L. Ostberg, P. H. Ehrlich, D. C. Wong, R. H. Miller, and R. H. Purcell. 1993. Markedly prolonged incubation period of hepatitis B in a chimpanzee passively immunized with a human monoclonal antibody to the a determinant of hepatitis B surface antigen. Proc Natl Acad Sci U S A. 90:3014–8.
39. Panda, S. K., S. K. Nanda, M. Zafrullah, I. H. Ansari, M. H. Ozdener, and S. Jameel. 1995. An Indian strain of hepatitis E virus (HEV): cloning, sequence, and expression of structural region and antibody responses in sera from individuals from an area of high-level HEV endemicity. J Clin Microbiol. 33:2653–9.
40. Persson, M. A., R. H. Caothien, and D. R. Burton. 1991. Generation of diverse high-affinity human monoclonal antibodies by repertoire cloning. Proc Natl Acad Sci U S A. 88:2432–6.
41. Purcell, R. H. 1996. Hepatitis E Virus. In B. N. Fields, Knipe, D. M., & Howley, P. M. (ed.), Fields Virology, 3rd ed. Lippinscott-Raven, Philadelphia.
42. Robinson, R. A., W. H. Burgess, S. U. Emerson, R. S. Leibowitz, S. A. Sosnovtseva, S. Tsarev, and R. H. Purcell. 1998. Structural characterization of recombinant hepatitis E virus ORF2 proteins in baculovirus-infected insect cells. Protein Expr Purif. 12:75–84.
43. Schlauder, G. G., G. J. Dawson, J. C. Erker, P. Y. Kwo, M. F. Knigge, D. L. Smalley, J. E. Rosenblatt, S. M. Desai, and I. K. Mushahwar. 1998. The sequence and phylogenetic analysis of a novel hepatitis E virus isolated from a patient with acute hepatitis reported in the United States [published erratum appears in J Gen Virol 1998 Oct.; 79(Pt 10):2563]. J Gen Virol. 79:447–56.
44. Schofield, D. J., and N. J. Dimmock. 1996. Determination of affinities of a panel of IgGs and Fabs for whole enveloped (influenza A) virions using surface plasmon resonance. J Virol Methods. 62:33–42.
45. Tam, A. W., M. M. Smith, M. E. Guerra, C. C. Huang, D. W. Bradley, K. E. Fry, and G. R. Reyes. 1991. Hepatitis E virus (HEV): molecular cloning and sequencing of the full-length viral genome. Virology. 185:120–31.
46. Thomas, D. L., P. O. Yarbough, D. Vlahov, S. A. Tsarev, K. E. Nelson, A. J. Saah, and R. H. Purcell. 1997. Seroreactivity to hepatitis E virus in areas where the disease is not endemic. J Clin Microbiol. 35:1244–7.
47. Thompson, J., T. Pope, J. S. Tung, C. Chan, G. Hollis, G. Mark, and K. S. Johnson. 1996. Affinity maturation of a high-affinity human monoclonal antibody against the third hypervariable loop of human immunodeficiency virus: use of phage display to improve affinity and broaden strain reactivity. J Mol Biol. 256:77–88.
48. Tomlinson, I. M., G. Walter, J. D. Marks, M. B. Llewelyn, and G. Winter. 1992. The repertoire of human germline VH sequences reveals about fifty groups of VH segments with different hypervariable loops. J Mol Biol. 227:776–98.
49. Tsarev, S. A., S. U. Emerson, G. R. Reyes, T. S. Tsareva, L. J. Legters, I. A. Malik, M. Iqbal, and R. H. Purcell. 1992. Characterization of a prototype strain of hepatitis E virus. Proc Natl Acad Sci U S A. 89:559–63.
50. Tsarev, S. A., T. S. Tsareva, S. U. Emerson, S. Govindarajan, M. Shapiro, J. L. Gerin, and R. H. Purcell. 1997. Recombinant vaccine against hepatitis E: dose response and protection against heterologous challenge. Vaccine. 15:1834–8.
51. Tsarev, S. A., T. S. Tsareva, S. U. Emerson, S. Govindarajan, M. Shapiro, J. L. Gerin, and R. H. Purcell. 1994. Successful passive and active immunization of cynomolgus monkeys against hepatitis E. Proc Natl Acad Sci U S A. 91:10198–202.
52. Tsarev, S. A., T. S. Tsareva, S. U. Emerson, A. Z. Kapikian, J. Ticehurst, W. London, and R. H. Purcell. 1993. ELISA for antibody to hepatitis E virus (HEV) based on complete open-reading frame-2 protein expressed in insect cells: identification of HEV infection in primates. J Infect Dis. 168:369–78.
53. Tsarev, S. A., T. S. Tsareva, S. U. Emerson, P. O. Yarbough, L. J. Legters, T. Moskal, and R. H. Purcell. 1994. Infectivity titration of a prototype strain of hepatitis E virus in cynomolgus monkeys. J Med Virol. 43:135–42.
54. Tsega, E., B. G. Hansson, K. Krawczynski, and E. Nordenfelt. 1992. Acute sporadic viral hepatitis in Ethiopia: causes, risk factors, and effects on pregnancy. Clin Infect Dis. 14:961–5.
55. Vijh-Warrier, S., E. Murphy, I. Yokoyama, and S. A. Tilley. 1995. Characterization of the variable regions of a chimpanzee monoclonal antibody with potent neutralizing activity against HIV-1. Mol Immunol. 32:1081–92.
56. Williamson, R. A., R. Burioni, P. P. Sanna, L. J. Partridge, C. F. d. Barbas, and D. R. Burton. 1993. Human monoclonal antibodies against a plethora of viral pathogens from single combinatorial libraries [published erratum appears in Proc Natl Acad Sci U S A 1994 Feb. 1; 91(3):1193]. Proc Natl Acad Sci U S A. 90:4141–5.
57. Winter, G., A. D. Griffiths, R. E. Hawkins, and H. R. Hoogenboom. 1994. Making antibodies by phage display technology. Annu Rev Immunol. 12:433–55.
58. Yin, S., R. H. Purcell, and S. U. Emerson. 1994. A new Chinese isolate of hepatitis E virus: comparison with strains recovered from different geographical regions. Virus Genes. 9:23–32.
59. Zhuang, H., X. Y. Cao, C. B. Liu, and G. M. Wang. 1991. Epidemiology of hepatitis E in China. Gastroenterol Jpn. 26 Suppl 3:135–8.

We claim:

1. An isolated neutralizing monoclonal antibody that is immunoreactive with hepatitis E virus (HEV), said antibody having heavy (H) chain immunoglobulin variable region amino acid sequence of SEQ ID NO: 1 and light (L) chain immunoglobulin variable region amino acid sequence of SEQ ID NO: 2.

2. The isolated neutralizing monoclonal antibody according to claim 1, wherein the heavy (H) chain immunoglobulin variable region amino acid sequence is encoded by nucleic acid sequence of SEQ ID NO: 5 and light (L) chain immunoglobulin variable region amino acid sequence is encoded by nucleic acid sequence of SEQ ID NO: 6.

3. A method of detecting HEV in a biological sample, comprising:
   (a) contacting the sample with the isolated monoclonal antibody according to claim 1 under conditions suitable to form a complex between the antibody and a HEV antigen; and
   (b) detecting the presence of said immune complex.

4. The method of claim 3, wherein the biological sample is selected from the group consisting of serum, saliva, plasma, bile, feces, lymphocytes, hepatocytes or other cells.

5. A pharmaceutical composition comprising the isolated monoclonal antibody of claim 1 and a pharmaceutical carrier.

6. A method of providing passive immunoprophylaxis to a mammal or passive immunotherapy to a mammal infected with hepatitis E virus comprising administering to said mammal a therapeutically effective amount of the isolated monoclonal antibody according to claim 1.

* * * * *

SEQUENCE LISTING

<160> NUMBER OF SEQ ID NOS: 44

<210> SEQ ID NO 1
<211> LENGTH: 126
<212> TYPE: PRT
<213> ORGANISM: Chimpanzee
<220> FEATURE:
<223> OTHER INFORMATION: Antibody

<400> SEQUENCE: 1

Glu Val Gln Leu Leu Glu Ser Gly Gly Ser Leu Val Gln Pro Gly Gly
 1               5                  10                  15

Ser Leu Arg Leu Ser Cys Ala Ala Ser Gly Phe Thr Phe Ser Asp Ser
            20                  25                  30

Trp Met His Trp Val Arg Gln Val Pro Gly Lys Gly Leu Glu Trp Asx
        35                  40                  45

Asp Thr Ile Ser Ser Asp Gly Asp Ser Thr Arg Tyr Ala Asp Ser Val
    50                  55                  60

Gln Gly Arg Phe Ile Ile Ser Arg Asp Asn Ala Lys Asn Thr Tyr Leu
65                  70                  75                  80

Leu Gln Met Asn Ser Leu Arg Val Glu Asp Thr Ala Val Tyr Tyr Cys
                85                  90                  95

Thr Arg Ser Pro Gln Tyr Cys Ser Thr Thr Arg Cys Asp Trp Ile His
            100                 105                 110

Tyr Asp Tyr Trp Gly Gln Gly Thr Leu Val Thr Val Ser Ser
        115                 120                 125

<210> SEQ ID NO 2
<211> LENGTH: 112
<212> TYPE: PRT
<213> ORGANISM: Chimpanzee
<220> FEATURE:
<223> OTHER INFORMATION: Antibody

<400> SEQUENCE: 2

Ala Glu Leu Thr Gln Ser Pro Ser Ser Leu Ser Ala Ser Val Gly Asp
 1               5                  10                  15

Arg Val Thr Ile Thr Cys Arg Ala Ser Gly Asp Val Gly His Tyr Leu
            20                  25                  30

Gly Trp Phe Gln Gln Lys Pro Gly Gln Ala Pro Lys Arg Leu Ile Tyr
        35                  40                  45

Ala Ala Ser Asn Leu Gln Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Leu Gln His Asn Ser Tyr Pro Trp Thr
                85                  90                  95

Phe Gly Gln Gly Thr Lys Leu Glu Ile Lys Arg Thr Val Ala Ala Pro
            100                 105                 110

<210> SEQ ID NO 3
<211> LENGTH: 131
<212> TYPE: PRT
<213> ORGANISM: Chimpanzee
<220> FEATURE:
<223> OTHER INFORMATION: Antibody

```
<400> SEQUENCE: 3

Glu Val Gln Leu Leu Glu Ser Gly Gly Ser Leu Val Gln Pro Gly Gly
 1               5                  10                  15

Ser Leu Arg Leu Ser Cys Ala Ala Ser Gly Phe Ile Phe Ser Asn His
            20                  25                  30

Ala Ile His Trp Val Arg Gln Thr Ser Asp Lys Gly Leu Glu Trp Val
        35                  40                  45

Ala Thr Ile Ser Gly Gly Gly Ala Thr Tyr Tyr Pro Asp Ser Val
    50                  55                  60

Lys Gly Arg Glu Thr Ile Ser Arg Asp Asn Ser Lys Asn Met Val Tyr
65                  70                  75                  80

Leu Gln Met Asn Ser Leu Arg Ala Glu Asp Thr Ala Val Tyr Tyr Cys
                85                  90                  95

Ala Lys Asp Val Leu Asn Val Phe Glu Ala Glu Arg Asn Tyr Gly Trp
            100                 105                 110

Ser Thr Gly Tyr Ser Phe Asp Tyr Trp Gly Gln Gly Thr Arg Val Thr
            115                 120                 125

Val Ser Ser
    130

<210> SEQ ID NO 4
<211> LENGTH: 117
<212> TYPE: PRT
<213> ORGANISM: Chimpanzee
<220> FEATURE:
<223> OTHER INFORMATION: Antibody

<400> SEQUENCE: 4

Ala Glu Leu Gln Met Thr Gln Ser Pro Ser Ser Leu Ser Ala Ser Val
 1               5                  10                  15

Gly Asp Arg Val Thr Ile Thr Cys Arg Ala Ser His Lys Met Tyr Asp
            20                  25                  30

Tyr Val Ser Trp Tyr His Gln Arg Pro Gly Glu Ala Pro Arg Leu Leu
        35                  40                  45

Ile Tyr Ala Ala Ser Thr Leu Gln Thr Gly Ala Pro Thr Arg Phe Ser
    50                  55                  60

Gly Ser Gly Ser Gly Thr Asp Phe Thr Leu Thr Ile Gly Gly Leu Gln
65                  70                  75                  80

Pro Glu Asp Phe Gly Thr Tyr Tyr Cys Gln Arg Ala Phe Gly Thr Gln
                85                  90                  95

Leu Thr Phe Gly Gly Gly Thr Lys Val Glu Ile Lys Arg Thr Val Ala
            100                 105                 110

Ala Pro Ser Ser Ser
        115

<210> SEQ ID NO 5
<211> LENGTH: 378
<212> TYPE: DNA
<213> ORGANISM: Chimpanzee
<220> FEATURE:
<223> OTHER INFORMATION: Antibody

<400> SEQUENCE: 5
gaggtgcagc tgctcgagtc tgggggaagc ttagttcagc cggggggtc  cctgagactc      60 tcctgtgcag cctctggatt caccttcagt gattcgtgga tgcactgggt ccgccaagtc    120
ccagggaagg ggctggagtg gtctcacgt atcagtagtg atggcgacag cacaagatac     180
```

```
gcggactccg tgcagggccg attcatcatc tccagagaca acgccaagaa cacactgtat      240
ctgcagatga atagtctgag agtcgaggac acggctgtgt attattgcac aagatcgccg      300
caatattgta gtactaccag gtgcgactgg attcactatg actactgggg ccaggggacc      360
ctggtcaccg tctcctca                                                    378

<210> SEQ ID NO 6
<211> LENGTH: 338
<212> TYPE: DNA
<213> ORGANISM: Chimpanzee
<220> FEATURE:
<223> OTHER INFORMATION: Antibody

<400> SEQUENCE: 6
gccgagctca cccagtctcc atcctcactg tctgcatctg taggagacag agtcaccatc      60
acttgtcggg cgagtcagga cgttggccat tatttaggct ggtttcagca gaaacctggg      120
caagccccta agcgcctgat ctatgctgca tccaatttgc agagtggggt cccatccagg      180
ttcagcggca gtggatctgg gacagaattc actctcacaa tcaggagcct ttcagcggca      240
gattttgcca cttattactg tctacaacat aatagttacc cttggacgtt gattttgcca      300
accaagctgg aaatcaaacg aactgtggct gcaccatc                              338

<210> SEQ ID NO 7
<211> LENGTH: 393
<212> TYPE: DNA
<213> ORGANISM: Chimpanzee
<220> FEATURE:
<223> OTHER INFORMATION: Antibody

<400> SEQUENCE: 7
gaggtgcagc tgctcgagtc tgggggaggc ttggtacagc cggggggtc cctaagactc        60 tcgtgtgcag cctctggatt catcttcagc aaccatgcca tacactgggt ccgccagact      120
tcagacaagg gctggagtg gtcgcaact attagtggtg gtggtggtgc acttattat         180 ccagactctg tcaagggccg attcaccatc tccagagaca attcgaagaa tatggtgtat      240
ctgcagatga acagcctgag agccgaggac acggccgtgt attactgtgc gaaagatgtt      300
ttaaatgttt tcgaggcgga acgaaactat ggttggagta ccgggtactc ctttgactac      360
tggggccagg gaacccgggt caccgtctcc tca                                   393

<210> SEQ ID NO 8
<211> LENGTH: 351
<212> TYPE: DNA
<213> ORGANISM: Chimpanzee
<220> FEATURE:
<223> OTHER INFORMATION: Antibody

<400> SEQUENCE: 8
gccgagctcc agatgaccca gtctccatcc tccctgtctg catctgtggg agacagagtc       60
actattacat gccgggcgag tcacaaaatg tacgactatg tgagttggta tcaccagaga      120
ccgggggaag cccctaggct cctgatctat gccgcctcaa ccttgcaaac tgggccccca      180
acaaggttca gtggcagtgg atctgggaca gacttcactc tcaccatcgg cggtctgcaa      240
cctgaagatt ttggaacata ttactgtcag cgtgctttcg ggacacagct caccttcggt      300
ggagggacca aggtggagat caaacgaact gtggctgcac catcttcttc a               351
```

-continued

```
<210> SEQ ID NO 9
<211> LENGTH: 30
<212> TYPE: PRT
<213> ORGANISM: Hepatitis E virus

<400> SEQUENCE: 9

Arg Val Ala Ile Ser Thr Tyr Thr Thr Arg Leu Gly Ala Gly Pro Val
 1               5                  10                  15

Ala Ile Ser Ala Ala Ala Val Leu Ala Pro Arg Ser Ala Leu
            20                  25                  30

<210> SEQ ID NO 10
<211> LENGTH: 30
<212> TYPE: PRT
<213> ORGANISM: Hepatitis E virus

<400> SEQUENCE: 10

Arg Val Ala Ile Ser Thr Tyr Thr Thr Ser Leu Gly Ala Gly Pro Val
 1               5                  10                  15

Ser Ile Ser Ala Val Ala Val Leu Ala Pro His Ser Ala Leu
            20                  25                  30

<210> SEQ ID NO 11
<211> LENGTH: 30
<212> TYPE: PRT
<213> ORGANISM: Hepatitis E virus

<400> SEQUENCE: 11

Arg Val Ala Ile Ser Thr Tyr Thr Thr Ser Leu Gly Ala Gly Pro Val
 1               5                  10                  15

Ser Ile Ser Ala Val Ala Val Leu Ala Pro His Ser Val Leu
            20                  25                  30

<210> SEQ ID NO 12
<211> LENGTH: 30
<212> TYPE: PRT
<213> ORGANISM: Hepatitis E virus

<400> SEQUENCE: 12

Arg Val Ala Ile Ser Thr Tyr Thr Thr Ser Leu Gly Ala Gly Pro Val
 1               5                  10                  15

Ser Ile Ser Ala Val Ala Val Leu Thr Pro His Ser Ala Leu
            20                  25                  30

<210> SEQ ID NO 13
<211> LENGTH: 30
<212> TYPE: PRT
<213> ORGANISM: Hepatitis E virus

<400> SEQUENCE: 13

Arg Val Ala Ile Ser Thr Tyr Thr Thr Ser Leu Gly Ala Gly Pro Val
 1               5                  10                  15

Ala Ile Ser Ala Val Ala Val Leu Ala Pro His Ser Ala Leu
            20                  25                  30

<210> SEQ ID NO 14
<211> LENGTH: 30
<212> TYPE: PRT
<213> ORGANISM: Hepatitis E virus
```

-continued

```
<400> SEQUENCE: 14

Arg Val Ala Ile Ser Thr Tyr Thr Thr Ser Leu Gly Ala Gly Pro Val
 1               5                  10                  15

Ser Ile Ser Ala Val Ala Val Leu Gly Pro His Ser Ala Leu
            20                  25                  30

<210> SEQ ID NO 15
<211> LENGTH: 30
<212> TYPE: PRT
<213> ORGANISM: Hepatitis E virus

<400> SEQUENCE: 15

Arg Val Ala Ile Ser Thr Tyr Thr Thr Ser Leu Gly Ala Gly Pro Thr
 1               5                  10                  15

Ser Ile Ser Ala Val Gly Val Leu Ala Pro His Ser Ala Leu
            20                  25                  30

<210> SEQ ID NO 16
<211> LENGTH: 17
<212> TYPE: PRT
<213> ORGANISM: Chimpanzee
<220> FEATURE:
<223> OTHER INFORMATION: Antibody

<400> SEQUENCE: 16

Ser Pro Gln Tyr Cys Ser Thr Thr Arg Cys Asp Trp Ile His Tyr Asp
 1               5                  10                  15

Tyr

<210> SEQ ID NO 17
<211> LENGTH: 22
<212> TYPE: PRT
<213> ORGANISM: Chimpanzee
<220> FEATURE:
<223> OTHER INFORMATION: Antibody

<400> SEQUENCE: 17

Asp Val Leu Asn Val Phe Glu Ala Glu Arg Asn Tyr Gly Trp Ser Thr
 1               5                  10                  15

Gly Tyr Ser Phe Asp Tyr
            20

<210> SEQ ID NO 18
<211> LENGTH: 6
<212> TYPE: PRT
<213> ORGANISM: Chimpanzee
<220> FEATURE:
<223> OTHER INFORMATION: Antibody

<400> SEQUENCE: 18

Gly Asn Ser Leu Asp Tyr
 1               5

<210> SEQ ID NO 19
<211> LENGTH: 18
<212> TYPE: PRT
<213> ORGANISM: Chimpanzee
<220> FEATURE:
<223> OTHER INFORMATION: Antibody
```

-continued

```
<400> SEQUENCE: 19

Gly Met Glu Tyr Tyr Asp Asn Trp Gly Lys Val Phe Leu Asp Ala Phe
1               5                   10                  15

Asp Leu

<210> SEQ ID NO 20
<211> LENGTH: 18
<212> TYPE: PRT
<213> ORGANISM: Chimpanzee
<220> FEATURE:
<223> OTHER INFORMATION: Antibody

<400> SEQUENCE: 20

Ser Glu Val Gly Gly Ser Trp Tyr Ile Asp Val Glu Ser Asn Trp Phe
1               5                   10                  15

Asp Pro

<210> SEQ ID NO 21
<211> LENGTH: 8
<212> TYPE: PRT
<213> ORGANISM: Chimpanzee
<220> FEATURE:
<223> OTHER INFORMATION: Antibody

<400> SEQUENCE: 21

Glu His Trp Arg Gln Leu Asp Tyr
1               5

<210> SEQ ID NO 22
<211> LENGTH: 18
<212> TYPE: PRT
<213> ORGANISM: Chimpanzee
<220> FEATURE:
<223> OTHER INFORMATION: Antibody

<400> SEQUENCE: 22

Gly Asp Pro Ile Glu Ala Met Ser Gly Gly Ser Trp Ile Glu Thr Phe
1               5                   10                  15

His His

<210> SEQ ID NO 23
<211> LENGTH: 9
<212> TYPE: PRT
<213> ORGANISM: Chimpanzee
<220> FEATURE:
<223> OTHER INFORMATION: Antibody

<400> SEQUENCE: 23

Ile Leu Met Phe Gly Val Leu Asn Ser
1               5

<210> SEQ ID NO 24
<211> LENGTH: 8
<212> TYPE: PRT
<213> ORGANISM: Chimpanzee
<220> FEATURE:
<223> OTHER INFORMATION: Antibody

<400> SEQUENCE: 24

Asp Arg Arg Gly Asp Phe Asp Phe
1               5
```

```
<210> SEQ ID NO 25
<211> LENGTH: 13
<212> TYPE: PRT
<213> ORGANISM: Chimpanzee
<220> FEATURE:
<223> OTHER INFORMATION: Antibody

<400> SEQUENCE: 25

Gly Ser Asn Trp Asn Ser Phe Tyr Tyr Tyr Met Asp Val
  1               5                  10

<210> SEQ ID NO 26
<211> LENGTH: 8
<212> TYPE: PRT
<213> ORGANISM: Chimpanzee
<220> FEATURE:
<223> OTHER INFORMATION: Antibody

<400> SEQUENCE: 26

Glu Gln Trp Arg Leu Tyr Asp Ser
  1               5

<210> SEQ ID NO 27
<211> LENGTH: 18
<212> TYPE: PRT
<213> ORGANISM: Chimpanzee
<220> FEATURE:
<223> OTHER INFORMATION: Antibody

<400> SEQUENCE: 27

Asp Arg Glu Val Tyr Pro Trp Asp Thr Tyr Phe Lys Pro Ser Tyr Phe
  1               5                  10                  15

Asp Phe

<210> SEQ ID NO 28
<211> LENGTH: 8
<212> TYPE: PRT
<213> ORGANISM: Chimpanzee
<220> FEATURE:
<223> OTHER INFORMATION: Antibody

<400> SEQUENCE: 28

Ser Gln Trp Arg Ala Leu Asp Leu
  1               5

<210> SEQ ID NO 29
<211> LENGTH: 8
<212> TYPE: PRT
<213> ORGANISM: Chimpanzee
<220> FEATURE:
<223> OTHER INFORMATION: Antibody

<400> SEQUENCE: 29

Asp Arg Arg Trp Glu Leu Glu Ile
  1               5

<210> SEQ ID NO 30
<211> LENGTH: 12
<212> TYPE: PRT
<213> ORGANISM: Chimpanzee
<220> FEATURE:
<223> OTHER INFORMATION: Antibody

<400> SEQUENCE: 30

Gly Asp His Thr Gly Tyr Val His Tyr Phe Asp Ser
  1               5                  10
```

```
<210> SEQ ID NO 31
<211> LENGTH: 9
<212> TYPE: PRT
<213> ORGANISM: Chimpanzee
<220> FEATURE:
<223> OTHER INFORMATION: Antibody

<400> SEQUENCE: 31

Val Thr Met Val Gly Val Leu Thr Asp
  1               5

<210> SEQ ID NO 32
<211> LENGTH: 14
<212> TYPE: PRT
<213> ORGANISM: Chimpanzee
<220> FEATURE:
<223> OTHER INFORMATION: Antibody

<400> SEQUENCE: 32

Glu Gly Cys Ser Gly Leu Ser Cys Tyr Gly Ser Phe Asp Arg
  1               5                  10

<210> SEQ ID NO 33
<211> LENGTH: 30
<212> TYPE: DNA
<213> ORGANISM: ARTIFICIAL SEQUENCE
<220> FEATURE:
<223> OTHER INFORMATION: Sequencing Primer

<400> SEQUENCE: 33
gcatgtacta gttgtgtcac aagatttggg                              30

<210> SEQ ID NO 34
<211> LENGTH: 21
<212> TYPE: DNA
<213> ORGANISM: ARTIFICIAL SEQUENCE
<220> FEATURE:
<223> OTHER INFORMATION: Sequencing Primer

<400> SEQUENCE: 34
attgcctacg gcagccgctg g                                       21

<210> SEQ ID NO 35
<211> LENGTH: 21
<212> TYPE: DNA
<213> ORGANISM: ARTIFICIAL SEQUENCE
<220> FEATURE:
<223> OTHER INFORMATION: Sequencing Primer

<400> SEQUENCE: 35
ggaagtagtc cttgaccagg c                                       21

<210> SEQ ID NO 36
<211> LENGTH: 21
<212> TYPE: DNA
<213> ORGANISM: ARTIFICIAL SEQUENCE
<220> FEATURE:
<223> OTHER INFORMATION: Sequencing Primer

<400> SEQUENCE: 36
acagctatcg cgattgcagt g                                       21
```

```
<210> SEQ ID NO 37
<211> LENGTH: 21
<212> TYPE: DNA
<213> ORGANISM: ARTIFICIAL SEQUENCE
<220> FEATURE:
<223> OTHER INFORMATION: Sequencing Primer

<400> SEQUENCE: 37
cacctgatcc tcagatggcg g                                              21

<210> SEQ ID NO 38
<211> LENGTH: 28
<212> TYPE: DNA
<213> ORGANISM: ARTIFICIAL SEQUENCE
<220> FEATURE:
<223> OTHER INFORMATION: Amplification Primer

<400> SEQUENCE: 38
atggcggtcg ctccggccca tgacaccc                                       28

<210> SEQ ID NO 39
<211> LENGTH: 33
<212> TYPE: DNA
<213> ORGANISM: ARTIFICIAL SEQUENCE
<220> FEATURE:
<223> OTHER INFORMATION: Amplification Primer

<400> SEQUENCE: 39
ctattaaatg gagatagcgt agccaccaac agc                                 33

<210> SEQ ID NO 40
<211> LENGTH: 33
<212> TYPE: DNA
<213> ORGANISM: ARTIFICIAL SEQUENCE
<220> FEATURE:
<223> OTHER INFORMATION: Amplification Primer

<400> SEQUENCE: 40
ctattagcgg aactcaagtt cgagggcaaa gtc                                 33

<210> SEQ ID NO 41
<211> LENGTH: 33
<212> TYPE: DNA
<213> ORGANISM: ARTIFICIAL SEQUENCE
<220> FEATURE:
<223> OTHER INFORMATION: Amplification Primer

<400> SEQUENCE: 41
ctattaagtc ggctcgccat tggctgagac gac                                 33

<210> SEQ ID NO 42
<211> LENGTH: 33
<212> TYPE: DNA
<213> ORGANISM: ARTIFICIAL SEQUENCE
<220> FEATURE:
<223> OTHER INFORMATION: Amplification Primer

<400> SEQUENCE: 42
ctattactgc gcgccggtcg caacattaac caa                                 33

<210> SEQ ID NO 43
<211> LENGTH: 31
<212> TYPE: DNA
<213> ORGANISM: ARTIFICIAL SEQUENCE
<220> FEATURE:
<223> OTHER INFORMATION: Amplification Primer
```

-continued

```
<400> SEQUENCE: 43
ctattaccga tgcccagcgg cattctcaac g                              31

<210> SEQ ID NO 44
<211> LENGTH: 31
<212> TYPE: DNA
<213> ORGANISM: ARTIFICIAL SEQUENCE
<220> FEATURE:
<223> OTHER INFORMATION: Amplification Primer

<400> SEQUENCE: 44
ctattatagc acagagtggg gggctaaaac a                              31
```